(12) United States Patent
Janik et al.

(10) Patent No.: US 9,134,227 B2
(45) Date of Patent: Sep. 15, 2015

(54) METHOD FOR DETERMINING POLYCYCLIC AROMATIC HYDROCARBON CONTAMINANT CONCENTRATION

(75) Inventors: Leslie Joseph Janik, South Australia (AU); Andreas Paul Loibner, Wolfsgraben (AT); Juergen Kattner, Vienna (AT); Eva Edelmann, Stockerau (AT)

(73) Assignees: UNIVERSITAT FUR BODENKULTER WIEN, Vienna (AT); Leslie Joseph Janik, South Australia (AU)

( * ) Notice: Subject to any disclaimer, the term of this patent is extended or adjusted under 35 U.S.C. 154(b) by 556 days.

(21) Appl. No.: 13/504,977

(22) PCT Filed: Oct. 21, 2010

(86) PCT No.: PCT/EP2010/065911
§ 371 (c)(1),
(2), (4) Date: Aug. 13, 2012

(87) PCT Pub. No.: WO2011/051166
PCT Pub. Date: May 5, 2011

(65) Prior Publication Data
US 2012/0318982 A1     Dec. 20, 2012

(30) Foreign Application Priority Data

Nov. 2, 2009 (EP) .................................. 09174729

(51) Int. Cl.
*G01J 5/02* (2006.01)
*G01N 21/3563* (2014.01)
(Continued)

(52) U.S. Cl.
CPC .......... *G01N 21/3563* (2013.01); *G01N 21/274* (2013.01); *G01N 21/314* (2013.01);
(Continued)

(58) Field of Classification Search
CPC ............ G01N 21/3563; G01N 21/359; G01N 21/3577; G01N 21/552; G01N 21/3504
USPC ...................................... 250/339.11
See application file for complete search history.

(56) References Cited

U.S. PATENT DOCUMENTS 8,759,775 B2 *  6/2014  Forrester et al. .......... 250/339.12
2003/0200040 A1 * 10/2003  Trygg et al. ..................... 702/85
(Continued)

OTHER PUBLICATIONS

Reeves et al., Mid-infrared Diffuse Reflectance Spectroscopy for the Quantitative Analysis of Agricultural Soils, 2001, J. Agric. Food Chem., vol. 49, pp. 766-772.*
(Continued)

*Primary Examiner* — Christine Sung
(74) *Attorney, Agent, or Firm* — Nixon & Vanderhye P.C.

(57) ABSTRACT

Method for determining polycyclic aromatic hydrocarbon (PAH) concentration in a solid state sample. The method includes exposing the sample to diffuse reflectance infrared spectroscopy, recording at least one spectroscopic parameter of infrared diffuse reflection of the sample, which is a signal obtained at one or more frequencies within a range of frequencies ($+/-10$ cm$^{-1}$) selected from the group consisting of 3000-3100 cm$^{-1}$, 740, 777, 814, 842, 1430, 1510, 1600, 4055-4056, 4642-4646, 5924, and 5951-5953 cm$^{-1}$, and performing data analysis by correlating the at least one spectroscopic parameter with variables of a trained multivariate calibration model related to PAH concentrations, thereby determining PAH concentrations in the sample.

16 Claims, 16 Drawing Sheets

(51) Int. Cl.
| | |
|---|---|
| *G01N 21/27* | (2006.01) |
| *G01N 21/31* | (2006.01) |
| *G01N 21/93* | (2006.01) |
| *G01N 21/3504* | (2014.01) |
| *G01N 21/3577* | (2014.01) |
| *G01N 21/359* | (2014.01) |
| *G01N 21/552* | (2014.01) |
| *G01N 21/35* | (2014.01) |

(52) U.S. Cl.
CPC ........... *G01N 21/93* (2013.01); *G01N 21/3504* (2013.01); *G01N 21/359* (2013.01); *G01N 21/3577* (2013.01); *G01N 21/552* (2013.01); *G01N 2021/3133* (2013.01); *G01N 2021/3155* (2013.01); *G01N 2021/3595* (2013.01); *G01N 2201/1293* (2013.01)

(56) References Cited

U.S. PATENT DOCUMENTS

2012/0153160 A1* 6/2012 Forrester et al. ........... 250/341.8
2012/0226653 A1* 9/2012 McLaughlin et al. ........... 706/52

OTHER PUBLICATIONS

Janik et al., Can mid infrared diffuse reflectance analysis replace soil extractions?, 1998, Australian Journal of Experimental Agriculture, vol. 38, pp. 681-696.*

Gordon et al., Characterization of Aerosol Organics by Diffuse Reflectance Fourier Transform Infrared Spectroscopy, 1988, Environ. Sci. Technol., vol. 22, pp. 672-677.*

Hudgins et al., Infrared Spectroscopy of Matrix Isolated Polycyclic Aromatic Hydrocarbons. 1. PAHs Containing Two to Four Rings, 1998, J. Phys. Chem. A, vol. 102, pp. 329-343.*

Kang, Minsun, Quantification of Soil Organic Carbon Using Mid- and Near-Drift Spectroscopy, Aug. 2002, pp. 1-74.*

Madari, B. E., et al; "Mid- and near-infrared spectroscopic assessment of soil compositional parameters and structural indices in two Ferralsols"; *Geoderma*, vol. 136, No. 1-2, pp. 245-259 (2006) XP025238053.

Bray, J.G.P., et al; "Diagnostic screening of urban soil contaminants using diffuse reflectance spectroscopy"; *Australian Journal of Soil Research*, vol. 47, No. 4, pp. 433-442 (2009) XP008120983.

Zimmermann, et al; "Quantifying soil organic carbon fractions by infrared-spectroscopy"; *Soil Biology and Biochemistry*, vol. 39, No. 1, pp. 224-231 (2006) XP005770678.

Viscarra, Rossel R.A., et al; "Visible, near infrared, mid infrared or combined diffuse reflectance spectroscopy for simultaneous assessment of various soil properties"; *Geoderma*, vol. 131, No. 1-2, pp. 59-75 (2006) XP025238263.

EPO Examination Report (Communication pursuant to Article 94(3) EPC), dated Jul. 4, 2014, issued in the European Counterpart Application No. 10768238.7 (4 pgs).

New Zealand First Examination Report dated Feb. 21, 2013, IP No. 599772 (2 pgs).

A Thesis by Kang, Misun; "Quantification of Soil, Organic Carbon Using Mid- and Near-Drift Spectroscopy" dated Aug. 2002 (74 pgs).

* cited by examiner

METHOD FOR DETERMINING POLYCYCLIC AROMATIC HYDROCARBON CONTAMINANT CONCENTRATION

This application is the U.S. national phase of International Application No. PCT/EP2010/065911 filed 21 Oct. 2010 which designated the U.S. and claims priority to European Patent Application No. 09174729.5 filed 2 Nov. 2009, the entire contents of each of which are hereby incorporated by reference.

This patent application claims priority from European Patent Application No. 09174729 titled "Method of determining Polycyclic Aromatic Hydrocarbon Contaminant Concentration" and filed 2 Nov. 2009, the entire content of which is hereby incorporated by reference.

FIELD OF THE INVENTION

The present invention relates to a device for determining polycyclic aromatic hydrocarbon (PAH) concentration in a solid state environmental sample using a multivariate regression model derived from diffuse reflectance infrared spectra and reference PAH concentrations of known samples. The method is capable of utilising diffuse reflectance infrared spectrometry data taken directly from a soil, rock or solid waste sample to predict PAH concentration in the sample.

BACKGROUND OF THE INVENTION

Most PAH substances are derived from incomplete combustion, coke production and tar processing as well as crude oil processing and storage. They are found in high concentrations at sites of former or present industrial activity. PAHs typically comprise several condensed aromatic rings (benzene) of varying physical-chemical characteristics and toxicity. The USEPA has identified 16 PAH congeneres as being the most hazardous ones. Due to their formation process, these 16 PAHs usually occur together with a large number of co-contaminants (hydrocarbons, alkylated and substituted aromatics, etc.) that have been considered as being of reduced risk. PAH compounds can become environmental contaminants in soils, with implications for human and environmental health, and may remain in the environment for extended periods. The level and type of PAH contamination is difficult, if not impossible, to determine by odour or visually unless gross contamination has occurred, so that rapid and inexpensive instrumental methods for the prediction of PAH compounds in soils is desirable for the identification of such hazards.

Urban areas with sites predominantly industrial in nature are increasingly being replaced by residential development, many of these sites, however, have been subjected to contamination from oils, fuels and other hydrocarbons, such as PAHs, and are therefore unsuitable for residential development because of failure to meet with environmental protection guidelines for acceptable concentrations of hazardous compounds. These contaminants can often be remediated to acceptable levels e.g. by removing contaminated soil but this process can incur significant costs and furthermore, delays caused by lengthy conventional PAH analysis in laboratories.

Current testing typically involves the extraction and instrumental analysis of the contaminant components in the soil extracts. Testing of PAHs in soils is usually carried out using high pressure liquid chromatography (HPLC) via solvent extraction of the PAH components from the soil samples, or by gas chromatography—mass spectroscopy (GC-MS), particularly for the more volatile PAH components, where analysis can take up to 40 minutes per run. This can be a major disadvantage of conventional analysis, considering the time and effort required for extraction and calibration, where a number of hours may be required for a result with chromatography.

A rapid, cost effective and potentially in-field method for predicting PAH concentration in a site would provide significant advantages in meeting the needs for contaminant quantification and monitoring. Infrared spectrometry, through the use of regression models, could offer a possible alternative approach for the rapid analysis of soil contaminants. Infrared spectroscopy distinguishes between chemical compounds by detecting the specific vibrational frequencies of molecular bonds, producing a unique infrared "spectral signature" thus enabling its identification and quantification. Whilst most existing infrared applications used to characterise hydrocarbon contaminants measure the spectra of infrared radiation transmitted through a sample cell containing a sample extract, considerable advantages can be achieved with reflection of the infrared radiation directly from the soil sample surface. One such method, diffuse reflectance infrared spectrometry in the mid-infrared (MIR) and visible-near infrared (vis-NIR), when coupled with multivariate chemometrics regression techniques such as partial least-squares (PLS), has been used for the rapid analysis of agricultural soil analysis for a large number of soil chemical and physical properties (Janik et al. 1998 Aust. J. Exp. Agric. 38:681-696; Reeves et al. 1999 Journal of Near Infrared Spectroscopy 7(3):179-193; and Cozzolino and Moron 2003 Journal of Agricultural Science. Volume: 140 Pages: 65-71 Part: Part 1). When using Fourier Transform based infrared spectrometers the method of diffuse reflectance is called DRIFT.

Madari et al. describe the mid- and near infrared spectroscopic assessment of soil compositional parameters and structural indices in two Ferralsols (J Geoderma 136(1-2) 245-259 (2006)). Bulk soil samples were analysed, e.g. for soil organic carbon. Absorption bands of carbon in organic bonds were found in the Mid-IR spectral range.

Infrared diffuse reflectance spectroscopy has been used to develop diagnostic screening tests for PAHs in soils using vis-NIR and an ordinal logistic regression method (Bray et al., Australian Journal of Soil Research 2009, 47:433-442). The above method differed from the present invention in that only threshold level classes of these soil contaminants were predicted, and that the regression models were based only on the loose correlation between soil composition and PAH concentration, rather than specific PAH peaks identified in the samples. Direct detection of PAH spectral peaks from NIR spectroscopy was not made by these authors and formal MIR analysis of PAHs was not carried out.

There are two potential problems with using diffuse reflectance infrared spectrometry for soil contaminant analysis. Some of the spectral peaks typically attributable to PAHs may occur in frequency regions having overlap with naturally-occurring soil organic matter (NOM), also called soil organic matter (SOM) or soil organic carbon (SOC), or with certain soil minerals. Also, due to the low concentrations usually encountered in contaminated samples, the sensitivity of the infrared for PAH predictions may be insufficient for accurate quantitative purposes.

It was the object of the present invention to provide a simple and rapid method with sufficient accuracy to determine PAH concentration in solid samples including soils.

SUMMARY OF THE INVENTION

The scope of the invention is described by the subject matter of the claims.

The subject matter of the following items are embodiments of the present invention:

1. The use of a device for determining PAH concentration in a solid state sample, which device comprises
   a) means for exposing the sample to diffuse reflectance infrared spectroscopy,
   b) detecting means for recording at least one spectroscopic parameter of infrared diffuse reflection of said sample, which is a signal obtained at one or more frequencies within a range of frequencies near (+/−10 cm$^{-1}$) those selected from the group consisting of 3000-3100 cm$^{-1}$, 740, 777, 814, 842, 1430, 1510, 1600, 4055-4056, 4642-4646, 5924 and 5951-5953 cm$^{-1}$, and
   c) computing means for performing data analysis by correlating the at least one spectroscopic parameter with variables of a trained multivariate calibration model related to PAH concentrations, thereby obtaining prediction of PAH concentrations in the sample.

The device is preferably pre-calibrated using the multivariate calibration model, ready to use for PAH determination.

2. Use according to item 1, wherein one or more signals are obtained at frequencies near those selected from the group consisting of 3022, 3047 and 3055 cm$^{-1}$.

3. Use of a device for determining PAH concentration in a solid state sample, which device comprises
   a) means for exposing the sample to DRIFT spectroscopy,
   b) detecting means for recording at least one spectroscopic parameter of MIR reflection of said sample, which is a signal obtained at frequencies ranging from 3000 to 3100 cm$^{-1}$, and
   c) computing means for performing multivariate data analysis by correlating the at least one spectroscopic parameter with variables of a trained system related to PAH concentrations, thereby obtaining quantitative calibration modelling and prediction of PAH in the sample.

4. Use according to item 3, wherein one or more further signals are obtained at frequencies selected from the group consisting of NIR and MIR ranges at about 5953 cm$^{-1}$ (NIR), 4646 cm$^{-1}$ (NIR), 4065 cm$^{-1}$ (NIR), 3047 cm$^{-1}$ (MIR) and 3022 cm$^{-1}$ (MIR).

5. Use according to any of items 1 to 4, wherein said multivariate data analysis is by multivariate regression analysis.

6. Use according to any of items 1 to 5, wherein said multivariate data analysis is by partial least square regression analysis.

7. Use according to any of items 1 to 6, wherein a system is used that is trained by employing either of
   a) a calibration data set,
   b) a calibration data set after removal of any outlier samples identified by the use of PLS score versus score plots, or
   c) selection of separate calibration and test sets.

8. Use according to item 7, wherein the separate calibration and test sets are selected for example using a PCA Euclidean distance leverage method.

9. Use according to any of items 1 to 8, which further comprises an internal calibration step performed by either training by cross-validation of the sample data or prediction of a test set from a selected calibration set.

10. Use according to item 9, which further comprises upgrading the calibration by adding further calibration samples of known PAH concentrations, to generate a recalibrated model for determining PAH concentration.

11. Use according to any of items 1 to 9, for calibration purposes to predict concentrations of either total PAH or of individual PAH compounds.

12. Use according to item 11, wherein a method of training a calibration system is employed, which comprises
   a) preparing a panel of diffuse reflectance infrared spectra obtained by solid state spectroscopy of different samples, having PAH concentrations at various levels in the range from 0 to 50,000 ppm, in some cases even up to 60,000 ppm, and
   b) correlating the spectra with the PAH concentration in the samples.

13. Use according to any of items 1 to 12, wherein the total PAH concentration is determined.

14. Use according to any of items 1 to 12, wherein the concentration of at least one individual PAH selected from polynuclear aromatics is determined.

15. Use according to any of items 1 to 14, which device comprises means for vis-NIR, NIR and/or MIR spectroscopy.

16. Use according to any of items 1 to 15, which device is a hand-held device or production line device.

17. A method of determining PAH concentration in a solid state sample, by using a device according to any of items 1 to 16.

18. Method according to item 17, wherein said sample is a soil, rock, solid waste sample, or a material derived from such sample, which sample is untreated as taken from the environment and optionally pretreated by drying, grinding and sieving.

19. Method according to item 17 or 18, which is an in-field or in-process determination method.

In a specific aspect, the present invention provides a device for determining PAH concentration in a solid state sample, comprising
   a) means for exposing the sample to DRIFT spectroscopy,
   b) detecting means for recording at least one spectroscopic parameter of MIR reflection of said sample, which is a signal obtained at frequencies ranging from 3000 to 3100 cm$^{-1}$, and
   c) computing means for performing multivariate data analysis by correlating the at least one spectroscopic parameter with variables of a trained system related to PAH concentrations, thereby obtaining quantitative prediction of PAH in the sample.

The device according to the invention preferably employs one or more further signals obtained at frequencies in the NIR and MIR ranges, such as at about 5953 cm$^{-1}$ (NIR), 4646 cm$^{-1}$ (NIR), 4065 cm$^{-1}$ (NIR), 3047 cm$^{-1}$ (MIR) and 3022 cm$^{-1}$ (MIR). Possible other preferred additional peaks are expected near 1600, 1510, 1430, 842, 814, 777 and 740 cm$^{-1}$.

According to a preferred embodiment the device employs said multivariate data analysis by partial least squares regression analysis.

Preferably the device according to the invention is used with a system that is trained by employing either of:
   a) a calibration data set,
   b) a calibration data set after removal of any outlier samples identified by the use of PLS or PCA score versus score plots, or
   c) selection of separate calibration and test sets, for example, using a PCA Euclidean distance leverage method.

It is preferred that the device according to the invention provides for the determination of the total PAH concentration and/or individual PAHs in the samples.

The preferred device according to the invention further comprises means for vis-NIR, NIR and/or MIR spectroscopy, such as means for Fourier-Transform and non Fourier Transform devices such as laser, filter and diode-array based instruments, and for field-portable and hand-held infrared spectrometers.

The invention specifically refers to the use of the device according to the invention for the specific purpose of determining a PAH concentration.

According to another aspect of the invention there is provided a method of training a calibration system for use with a device according to the invention, which comprises a) preparing a panel of DRIFT spectra obtained by solid state DRIFT spectroscopy of different samples, having PAH concentrations at various levels in the range from 0 to 50,000 ppm, and b) correlating the spectra with the PAH concentration in the samples.

In a preferred embodiment said spectra range comprises vis-NIR and/or MIR frequencies.

Another aspect of the invention refers to a method of determining PAH concentration in a solid state sample, comprising the following steps a) exposing the sample to DRIFT spectroscopy to obtain at least one spectroscopic parameter of MIR reflection from said sample, which is a signal obtained at a frequency within the 3000 to 3100 $cm^{-1}$ range, and b) correlating the at least one spectroscopic parameter with variables of a trained system, thereby obtaining quantitative calibration and prediction of total PAH in the sample.

In a preferred determination method according to the invention said trained system is obtainable by a training method according to the invention.

Preferably said sample is a soil, rock or solid waste sample, or materials derived from such samples, which is optionally pretreated by drying, grinding and sieving.

In a preferred aspect the method according to the invention employs a spectroscopic parameter, which is a signal obtained at a MIR frequency ranging from 3000 to 3100 $cm^{-1}$.

The preferred method according to the invention further comprises an internal calibration step, performed by either cross-validation of the sample data or by prediction of a test set from a calibration set selected by, for example, PCA (principle component analysis) leverage based on Euclidean distances.

Another preferred method according to the invention further comprises upgrading the calibration by adding further calibration samples of known PAH concentrations, and repeating steps a) and b) above to generate a recalibrated model for determining PAH concentration.

DETAILED DESCRIPTION OF THE INVENTION

Figure 1:
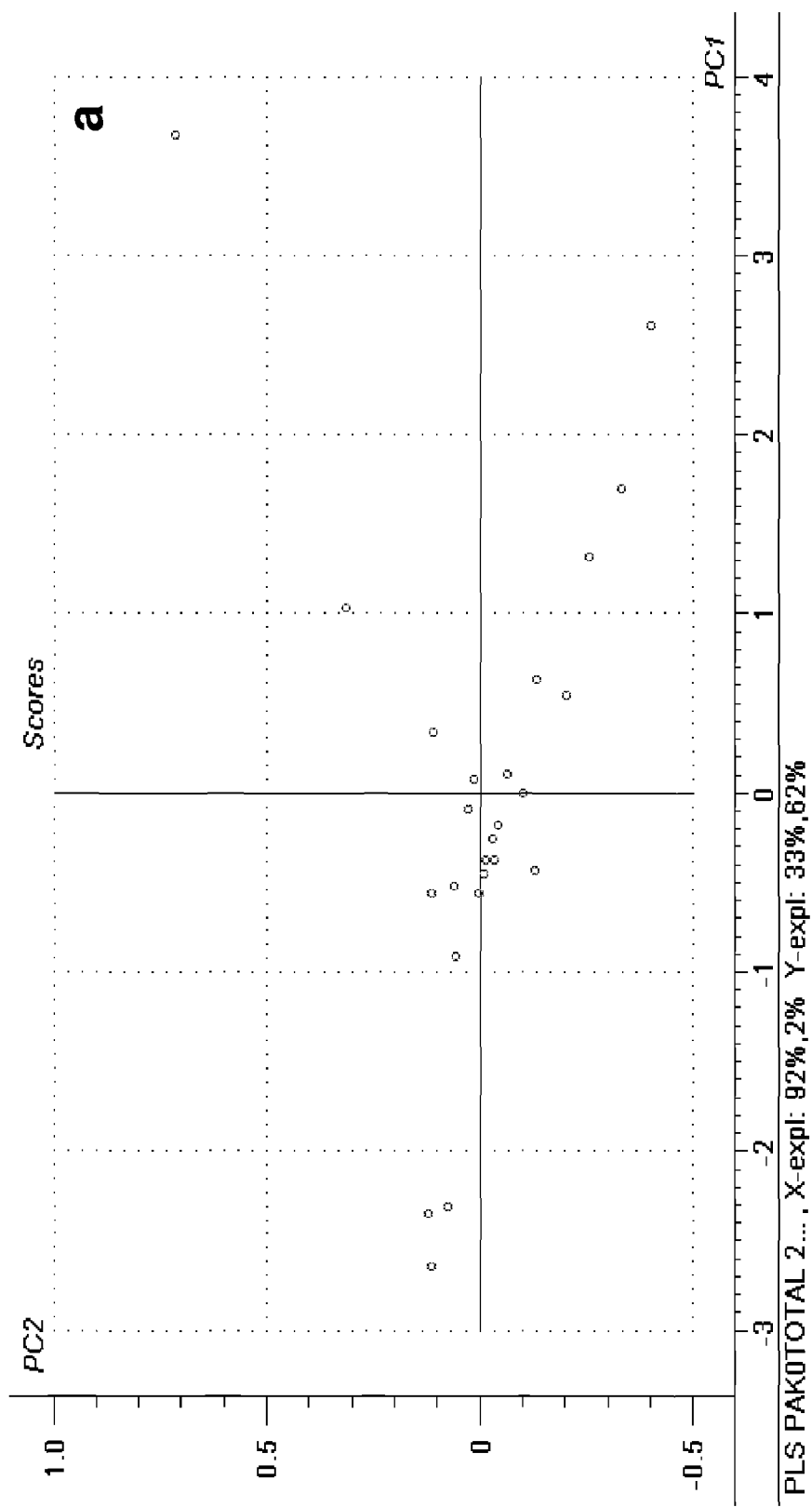
FIG. 1: PLS cross-validation regression plots of (a) score-2 versus score-1, (b) regression coefficients, (c) residual variance for each factor, and (d) cross-validation predicted total PAH for the full soil set in the range 0-40,000 mg/kg (ppm).
Figure 1:
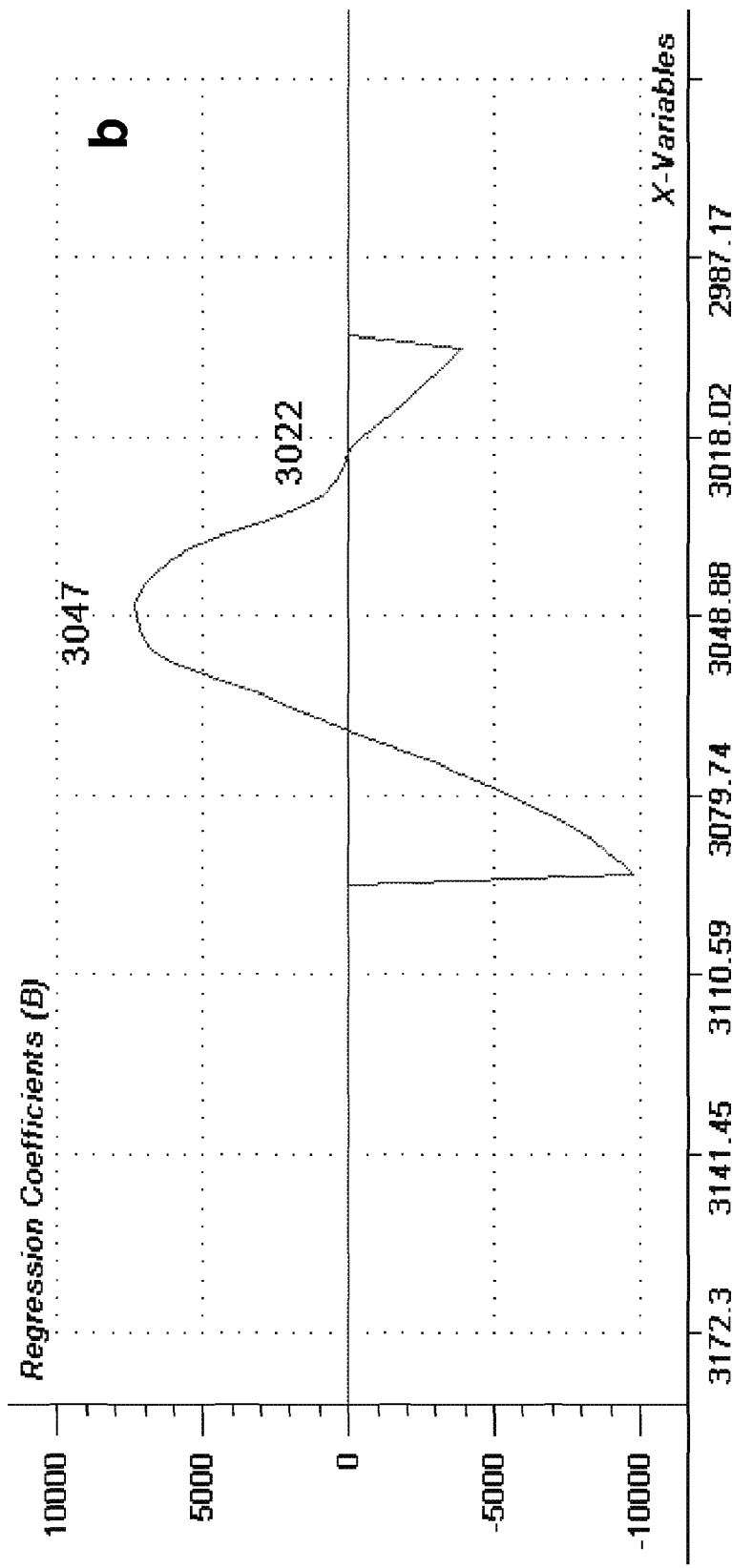
Figure 1:
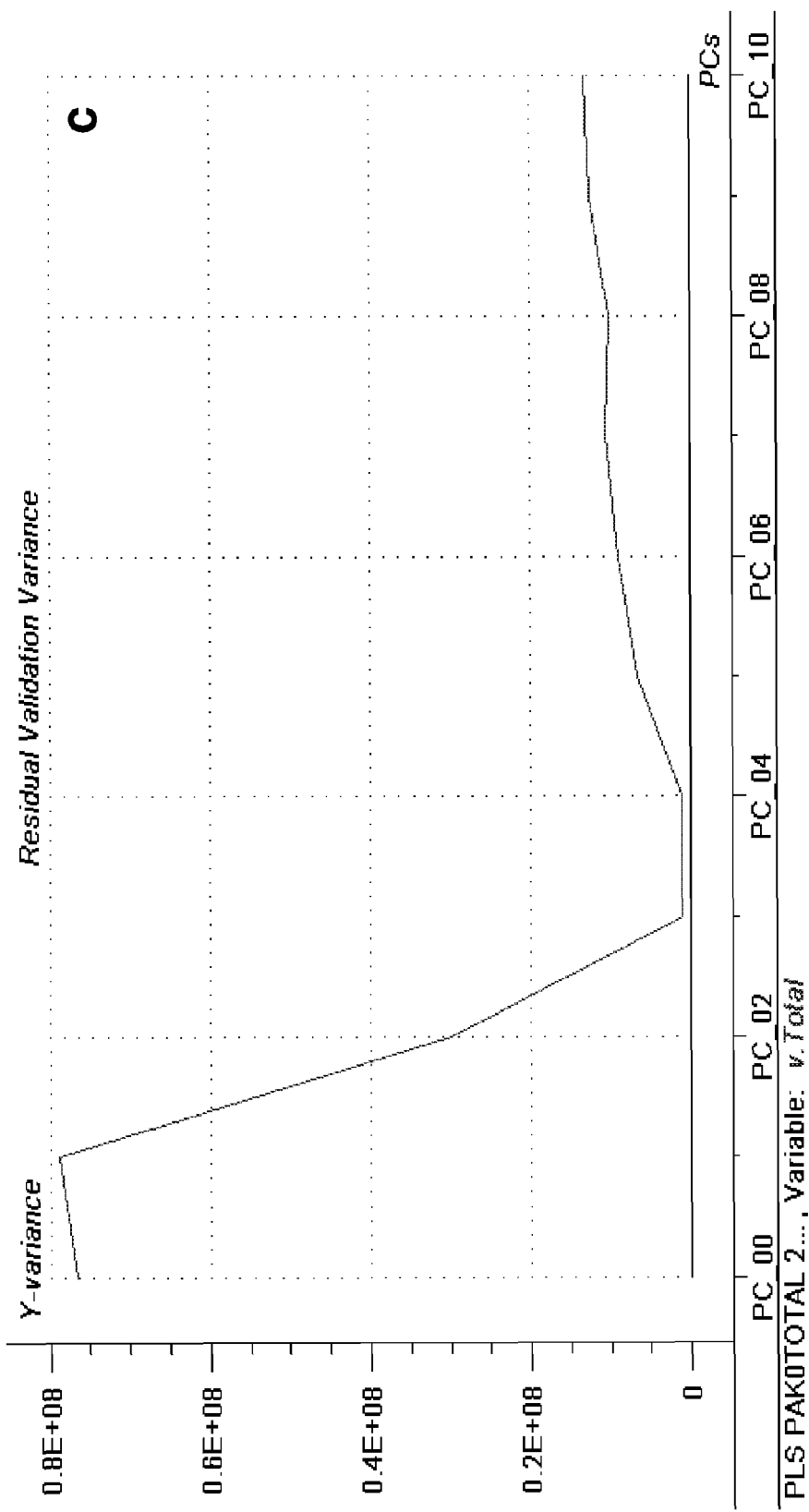
Figure 1:
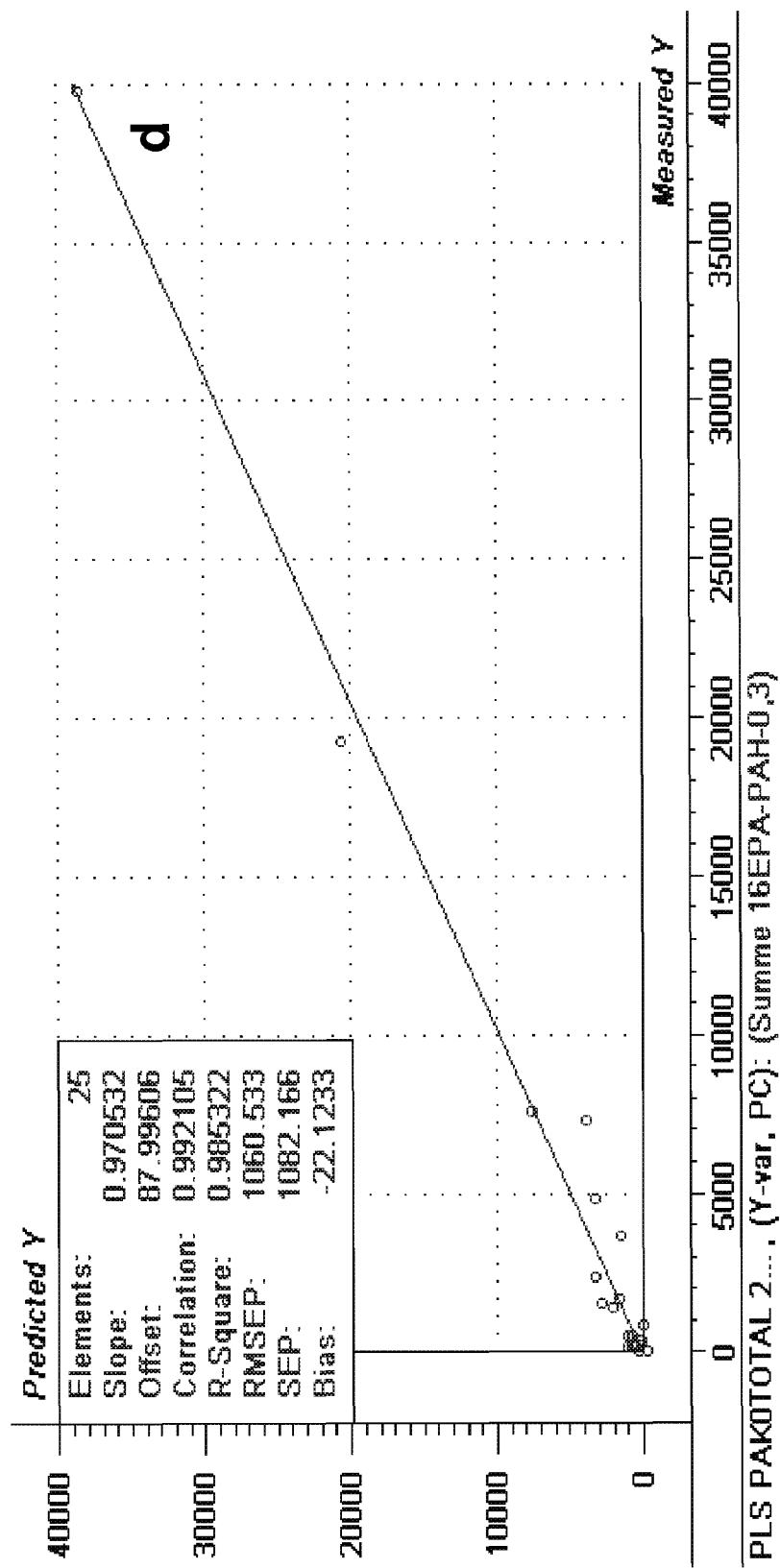

The term "polycyclic aromatic hydrocarbons" (PAHs), as used herein in relation to a potentially contaminated sample, is to be preferably understood to refer to substances comprising of up to 16 aromatic compounds considered to belong to the most important components of the group known as "polynuclear aromatics", i.e. naphthalene, acenaphthylene, acenaphthene, fluorene, phenanthrene, anthracene, fluoranthene, pyrene, benzo(a)anthracene, chrysene, benzo(b)fluoranthene, benzo(k)fluoranthene, benzo(a)pyrene, dibenz(a,h)anthracene, benzo(g,h,i)perylene and indeno(1,2,3-c,d)pyrene.

The term "infrared" (IR) used herein in relation to radiation absorbed by molecules in the frequency ranges 13,000-4,000 $cm^{-1}$ (near infrared—NIR) and 4,000-400 $cm^{-1}$ (mid-infrared—MIR). In infrared spectroscopy, a spectrum may comprise a series of absorbance peaks according to the vibrational modes of the component molecules, giving a unique "signature" of the absorbing compounds. The term "diffuse reflectance infrared" used herein, in relation to the recorded IR spectrum, refers to a combination of the IR radiation reflected by diffuse reflectance from the sample surfaces, which is known as "specular" reflectance and from within particles in the first few micrometres of the surfaces of the solid sample, i.e."volume" reflectance. As used herein, all wavenumbers are expressed in $cm^{-1}$ units, and spectral intensities as pseudo absorbance units (A) wherein A=Log Reflectance$^{-1}$.

The term "diffuse reflectance infrared spectra" as used herein shall refer to spectra obtained as a result of diffuse reflectance spectroscopy using infrared light. Particular diffuse reflectance infrared spectra are obtained by Fourier transform infrared spectroscopy (FTIR), which is then called diffuse reflectance infrared Fourier transform (DRIFT) spectra. FTIR spectrometers usually employ a computer dedicated to controlling the spectrometer, collecting the data, doing the Fourier transform and presenting the spectrum. Hence, the invention that employs diffuse reflectance infrared spectra, is herein always understood to particularly refer to DRIFT spectra.

With respect to the specific frequencies of the diffuse reflectance infrared spectra as used according to the invention the term "about" or "near" a specific frequency shall mean +/-10 $cm^{-1}$, preferably +/-5 $cm^{-1}$, more preferred +/-3 $cm^{-1}$ or even +/-2 $cm^{-1}$ or +/-1 $cm^{-1}$. The term shall particularly include the exact frequency value.

The present invention thus relates to a multivariate model based on diffuse reflectance infrared spectroscopy of solid state, e.g. whole-soil samples and reference PAH data, in particular a partial least squares (PLS) PAH prediction model. This model is capable of using the diffuse reflectance infrared spectrum taken directly from the surface of an unknown soil sample to predict its PAH concentration.

Diffuse reflectance infrared spectra and reference PAH data for known samples are used to generate PLS prediction models for PAH concentration, and then the models are used to predict the concentration of total and/or individual PAHs in unknown samples from their diffuse reflectance infrared spectra as inputs.

The PLS diffuse reflectance infrared method has not been used before to determine PAH concentrations in solid state samples. The use of diffuse reflectance infrared spectroscopy on samples, such as whole soils, without extraction by solvents, provides a great advantage of the method according to the invention, which is the first known application of this method for the determination of the PAH concentrations with reasonable sensitivities. This is due largely to the use of PLS regression and the sensitivity of diffuse reflectance infrared to PAH compounds. By the inventive selection of the specific MIR frequencies, according to the invention, spectral information specific to the aromatic =C—H function groups in PAH was surprisingly identified near 3100-3000 cm$^{-1}$, in particular two main peaks, one within the range of 3052-3042, most preferably at about 3047, and the other within the range of 3027-3017, most preferably at about 3022 cm$^{-1}$, that allowed for the modelling and prediction of PAHs with an accuracy of PAH determination which is useful for quantification, i.e. the determination of PAH concentration, either quantitatively or semi-quantitatively.

Further specific frequencies which were found to be specifically relevant for the determination of total or individual PAH have been identified near 740, 777, 814, 842, 1430, 1510, 1600, 4055-4056, 4642-4646, 5924, and 5951-5953 cm$^{-1}$, e.g. as exemplified below.

In a particular aspect, the present invention provides a method of predicting PAH concentrations in a sample of unknown total PAH concentration or individual PAH component concentration (the unknown sample), said method comprising the steps of:

(i) separately subjecting samples in a set of calibration samples with known PAH concentrations to IR radiation, (ii) separately detecting the diffusely reflected IR spectrum from the samples of known PAH concentrations, (iii) setting up, training and optimising the spectral ranges and PLS parameters for the calibration models from the spectral data and the reference PAH calibration data, preferably omitting any sample outliers.

(iv) selecting a PLS calibration model (the predictive model) for predicting PAH concentrations based on the PLS calibration model, (v) subjecting the unknown sample to the same infrared (IR) radiation, (vi) collecting the diffuse reflectance infrared spectrum, for example DRIFT, from the unknown sample, (vii) applying the PLS calibration model to the diffuse reflectance infrared spectrum from the unknown sample; and thereafter (viii) predicting PAH concentration in the unknown sample.

Step (i) may be conducted directly on the sample (i.e. without any pre-processing or pre-treatment of the sample), but for some samples, it may be preferable to dry (e.g. to a water content of less than 20%), crush, grind and/or sieve the sample prior to exposure to the IR radiation, so as to ensure sample uniformity and full exposure of material within the sample aggregates to the IR beam. According to a preferred method, e.g. for samples using laboratory-based infrared equipment, samples such as soil, rock or solid waste samples, or materials derived from such samples, are sieved <2 mm, more preferred <1 mm. The particle size characteristics of the sample may affect the "spectral definition" and apparent intensity of the reflected IR signal of the adsorbed PAHs so that sample grinding or other physical pre-process must be taken into account.

For in-field measurements hand-held infrared instruments may be preferable, which provide for scanning samples in-situ, e.g. within the environment, or ex-situ, such as taken from the environment, without any pre-processing, which may speed up analysis. Therefore, a hand-held spectrometer is preferably used to take the IR spectrum and read-outs onsite without the need to draw samples or perform any sample processing. Typical hand-held devices are known e.g. for onsite detection of oil contamination in soil or for oil exploration purposes. These devices may be adapted for the purpose of the invention.

Further preferred devices are production-line devices, e.g. devices for process controls, such as to determine contaminants or undesired PAHs in solid materials. Exemplary process controls by the inventive methods are useful as in-process control, for instance, in waste processing, smoke or combustion control, where solid materials, such as waste, soot or carbon black is analysed for a PAH concentration in an automated or semi-automated way.

Furthermore, it has been found that while the presence of slight to moderate amounts of moisture can be dealt with by the PLS method, the presence of excessive water may act as a "mirror" on the sample surface thereby causing distortion or reduction of the IR signals. Therefore, for some samples, it may be preferred to partially dry the sample prior to subjecting the sample to IR scanning. Drying the sample is preferably conducted in air at a temperature of less than 40° C. so as to avoid the volatilisation or modification of the PAHs. More preferably, the drying of the sample is conducted at room temperature.

Preferably, the use of the present invention is intended for the prediction of total PAH concentration in a solid sample, although it may also be applied to individual PAHs. Aromatic compounds, typical of PAHs, usually give characteristic =C—H vibrations near 3200-3000 cm$^{-1}$ and aromatic ring vibrations near 1580-1600 cm$^{-1}$, 1500 cm$^{-1}$ and 1360 cm$^{-1}$. However, some common sample matrices, such as soils often comprise mineral components or NOM materials, including aromatic NOM such as char and lignin that may cause interference in performing IR analysis of PAH. In particular, these materials can mask or hide regions of the IR spectrum in which aromatic molecular signals of contaminants are located, preventing the differentiation or identification of useful peaks. Quartz (i.e. sand) and clays can give strong IR signals below 2000 cm$^{-1}$ near 1600 cm$^{-1}$ due to silicate Si—O and Al—OH combination/overtone vibrations. In addition, water can absorb near 1630 cm$^{-1}$. Natural soil organic matter (NOM) usually contains proteins and amides with —OC—NH groups with strong peaks at 1680 cm$^{-1}$ and 1530 cm$^{-1}$, and carboxylate (COO—) groups or carboxyl (—COOH) groups with frequencies near 1600 cm$^{-1}$ and 1400 cm$^{-1}$, and near to 1720 cm$^{-1}$, respectively. The methods of the present invention are therefore based upon PLS modelling techniques capable of discriminating between PAH and components of the sample.

In step (ii) of the above described method, spectra are collected from almost the entire diffuse reflectance infrared spectral region. According to the invention, steps (iii) and (iv) may be conducted on specific spectral regions with high correlation with the PAH concentrations, thus basing the PLS models on only these regions such as the selected MIR peaks according to the invention at 3100-3000 cm$^{-1}$, optionally together with other peaks in the NIR, or alternatively peaks in the NIR range separate from MIR peaks, which would be associated with the aromatic =C—H functional group. For example, it turned out that the PAH sensitive peaks near 3047 cm$^{-1}$ avoid substantial overlap with those of naturally-occurring materials in soils. It may as well be preferred to include further peaks within the NIR and MIR ranges such as at about 5953 cm$^{-1}$ (NIR), 4646 cm$^{-1}$ (NIR), 4065 cm$^{-1}$ (NIR), 3047 cm$^{-1}$ (MIR) and 3022 cm$^{-1}$ (MIR). Possible other peaks are expected near 1600, 1510, 1430, 842, 814, 777 and 740 cm$^{-1}$, in particular when determining high PAH concentrations up to 40,000 ppm, for the purpose of multivariate analysis.

PLS models from regions outside this range are likely to be correlated more with naturally occurring sample components rather than PAH compounds and are therefore expected to lead to less accurate performance. Some variation in the exact location of a PAH peak may differ from that reported in the literature.

The basis of determining the PAH concentration usually is a trained calibration model, preferably achieved through training on the full calibration data set, after removal of any outlier samples identified by the use of PLS score versus score plots, or selection of separate calibration and test sets such as by using a PCA Euclidean distance leverage method.

Preferably, the step of selecting the number of PLS factors, which preferably is the optimum number of PLS factors, in (iv) and generating a partial least squares (PLS) predictive model for PAH concentration based on the selected number of factors involves:
 (i) Constructing a PLS model based on specified spectral regions and corresponding PAH reference data,
 (ii) Optionally removing any outlier samples from the calibration set according to indication of outliers in the PLS score-versus-score map,
 (iii) Finding the minimum total residual prediction error for all calibration samples for increasing PLS latent variables (factors),
 (iv) Saving the model giving the smallest minimum total residual prediction error for predictions.

Steps (i-ii) are repeated for a number of modelling options and frequency regions.

Further samples may be added to the calibration model at later dates to give the model a greater capacity to deal with unknown samples having new or substantially different composition to the existing calibration. Alternatively, outlier samples can be identified according to their distance from neighbouring samples in PCA or PLS score versus score plots, and removed prior to calibration. Calibration training and testing is often achieved by a method called cross-validation where each sample in the calibration set is predicted from all the others. Calibrations based upon small number of samples may be unstable and incapable of achieving a fit with the model parameters, leading to poor predictions. More samples characteristic of the new unknowns may therefore need to be added to the model. PLS models from a large number of diverse further samples are expected to be more robust, and therefore may be more broadly applicable to a variety of unknown sample types. Indeed, it is expected that calibrations performed on a very high number of further samples may generate a universally applicable predictive model. In contrast, a relatively few number of calibration samples may be sufficient to model a certain region with many samplings due to the similarities of the underlying sample matrix in all the samples in the site. Alternatively, a method of selecting separate calibration and test samples can be carried out, for example based on ranking the samples according to their PCA Cartesian distance leverages. Even with a low number of calibration samples, preferably 4 to 6 samples, the robustness and stability of the PLS models can thus be tested. In some cases, the PCA Cartesian distance leverage method has been shown to be an efficient method for generating a smaller and more robust calibration model than the usual full cross-validation method.

In another aspect, the present invention provides a method for generating the PLS model. For example, unknown uncontaminated samples, perhaps from the site being analysed, may be spiked with known concentrations of PAH to provide calibration samples of known PAH concentration. A model thus derived may be generated by spiking samples of similar composition, e.g. samples from the same site that are known not to contain further hydrocarbons or co-contaminants, with known concentrations of PAHs.

This method is particularly useful for training a calibration system for use with a device according to the invention. Specifically, a panel of diffuse relectance infrared spectra obtained by solid state diffuse relectance infrared spectroscopy of different samples is employed characterized by PAH concentrations at various levels in the range from 0 to 50,000 ppm, in some cases even up to 60,000 ppm. Preferably the sensitivity of a robust method according to the invention for total PAH and in some cases individual PAH determination is such to quantitate values of at least 1000 ppm, 500 ppm, 300 ppm, 200 ppm, more preferred at least 150 ppm, still it is preferred to determine quantities with a sensitivity of at least 100 ppm, 50 ppm or 25 ppm, or even lower than this limit. For determining individual PAHs the sensitivity is typically even less than 25 ppm, specifically less than 20 ppm, 15 ppm, 10 ppm, 5 ppm, 2.5 ppm or 1.5 ppm, even down to 0.1 ppm is possible.

It is preferable to account for a range of samples, such as of different soil types, for example calcareous soils, sandy soils and heavy clay soils, and in particular those soil samples with high NOM concentration, e.g. 5-25%, which enables the broad applicability of the PAH quantification in a variety of soil samples.

Methods may be carried out by exporting the spectra into chemometrics software, eg. Unscrambler™ Ver. 9.80 software (CAMO Software AS, Oslo, Norway). PLS options such as full "leave-one-out" cross-validation (Geladi and Kowalski 1986, Analytica Chimica Acta 185:1-17), baseline correction and other pre-processing options are available with the use of these and similar software applications in an attempt to improve the models.

As used herein, the performance of cross-validation regression was expressed in terms of the coefficient of determination ($R^2$) and root mean square error of cross-validation (RMSECV), whereas RMSECV represents a measure of the standard error (SE) of the method. The selection of optimal regions of the infrared may be determined by performing repetitive cross-validations of the predictive model with changing frequency ranges and selecting the model giving the highest $R^2$ and lowest RMSECV. Care must be taken to use the fewest number of PLS factors and thus avoid overfitting the models prior to undertaking steps (v) to (vii).

Alternatively, the calibrated model may be used in place of steps (i) to (iv) in methods of the second aspect for further future calibration of the model. Each additional calibration step may generate a more robust model which should provide a lower error of prediction.

While the diffuse reflectance, in particular the DRIFT methods of the present invention, may be suitable for providing a quantitative prediction of PAH concentrations in an unknown sample, they may also be suitable for providing a semi-quantitative assessment of polyaromatic concentration in an unknown sample, thereby enabling classing of PAH contamination for threshold limits by diagnostic screening of contaminants.

In accordance with the method of the invention it is in some cases preferred to determine individual PAHs, such as those selected from the polynuclear aromatics. Therefore, a correlation with concentrations of the individual PAHs is provided at specific frequencies, such as those exemplified below. The system is then preferably calibrated with the individual PAHs.

The methods described herein may be applied to the spatial characterisation of a site, including the mapping of PAH contamination throughout the site, for example the distribution of PAH leaking from a point source such as a fuel storage supply or tar pits.

The methods also may be applied to determine the PAH concentration together with, or in the presence of, other contaminants such as mineral oil or petroleum contaminants, employing frequencies known in the art for those other contaminants, preferably in a quantitative way. The combination method is particularly suitable before sanitizing contaminated samples, such as soils.

IR spectroscopy using diffuse reflectance according to the invention delivers a result of quantification within a few minutes. Easy to use devices preferably comprise laser, infrared or LED sources to provide for the specifically selected IR range only, thereby employing the method according to the invention with a surprisingly good sensitivity. Specific devices may be field-portable and hand-held spectrometers designed to be used for rapid analysis in field sites using untreated samples.

Thus, it is for the first time possible to quantitatively determine PAH concentrations using just one calibration set, e.g. with a standard error of less than 15%, preferably less than 10%, 5%, 2.5% or 1%, even down to 0.5% and maximum range of approximately 0-50,000 ppm, even up to 60,000 ppm, using only highly specific frequency ranges, near real-time, and in the future possibly at some distance from the spectrometer. In particular, the present invention is directed at describing a diffuse reflectance PLS based method for predicting PAH contaminant concentrations in samples, suitable for a quantitative accuracy of the calibration depending on the PAH concentration range, e.g. a standard error of less than 300 ppm for total PAH, at contaminating concentrations of up to 2500 ppm, and a standard error of less than 1000 ppm PAH at contaminating concentrations of up to 40,000 ppm, In particular, the present invention is directed at describing a diffuse reflectance PLS based method for predicting PAH contaminant concentrations in samples, suitable for a quantitative standard error for total PAH of less than 1000 ppm, 500 ppm, 300 ppm or 200 ppm, more preferred less than 150 ppm, still it is preferred to determine quantities with a standard error of prediction of less than 100 ppm, 50 ppm, 25 ppm or even lower than this limit. For individual PAHs the quantitative standard error of the inventive method specifically is even less than 25 ppm, specifically less than 20 ppm, 15 ppm, 10 ppm, 5 ppm, 2.5 ppm or 1.5 ppm, even down to 0.5 ppm is possible.

The present invention is further illustrated by the following examples without being limited thereto.

EXAMPLES

Example 1

PLS Prediction of Total PAH in Soils

Assessment of the use of mid-infrared spectroscopy and partial least-squares analysis for the prediction of PAH concentration in soils.

SUMMARY

This is an example demonstrating the prediction of PAH concentrations (as measured using HPLC) in neat, whole soils from mid-infrared (MIR) DRIFT spectra using partial least-squares (PLS) chemometrics. By the PLS analysis, using soil DRIFT spectra as calibration inputs, it can be shown that DRIFT spectroscopy may offer some potential for prediction of total PAH concentrations more rapidly and at lower cost than with HPLC.

Spectral frequencies for at least two DRIFT spectral peaks near 3047 to 3022 $cm^{-1}$ due to the =C—H aromatic functional group, were used as the independent variable inputs to the PLS models used for cross-validation regression. Cross-validation regression for 25 samples resulted in an $R^2$=0.99, and an RMSECV=1061 ppm for the full-range concentration range of 0-40,000 ppm. Reduction of the concentration ranges, first to 20 samples in the range 0-4,000 ppm and then 19 samples in the range 0-2500 ppm, reduced the RMSECV to 498 ppm (3-factors) and 287 ppm (4 factors) respectively. A further reduction in RMSECV to 216 ppm for the 0-2500 ppm range could be achieved using 5 factors.

The robustness and stability of the PLS models was tested using a very small set (five) of carefully selected calibration samples to derive the calibration model in order to perform a "true" prediction of the remaining samples as test samples rather than using cross-validation. The basis for selection was a ranking of samples according to spectral Euclidean distance leverages (according to an Unscrambler application) derived from a principal components analysis (PCA) of the input data. The accuracy of the "true" prediction was similar to that of cross-validation for some analyses, with results sometimes better and sometimes slightly worse than for full "leave-one-out" cross-validation.

Introduction

Maximum levels of contamination levels for environmental, residential and industrial sites are controlled by government legislation, and require that concentrations are measured within a specific time frame. This often raises problems due to high cost and lengthy time constraints. Diffuse reflectance mid-infrared Fourier transform (DRIFT) spectroscopy has been shown to be a rapid and relatively inexpensive surrogate to traditional reference laboratory methods for the determination of soil properties from their spectra using partial least squares (PLS) regression chemometrics. There is therefore the possibility that this technology could be applied to the prediction of total PAH concentrations in soils, and furthermore used to indicate whether the levels of PAHs are below, close to, or above critical PAH levels.

For some countries (e.g. Austria), the level for total PAH can be as low as 300 ppm before the contaminated soil can be disposed of. Environmental trigger values are even lower for e.g. residential purposes and soils exceeding such concentrations are classed as "contaminated" with regard to health. Resulting remediation measures involve very frequently removal of contaminated soil, treatment to reduce total PAH concentration below disposal limit, and finally deposition at a controlled landfill.

Different critical levels are legislated for the individual 16 PAH compounds that are associated with soil contamination, and in some cases could be very low and below the detection limit of an infrared-based method. However, the total PAH concentrations, and in some cases concentrations of individual PAHs, have been shown to be high enough in contaminated soils to be above the detection limits characteristic of organic compounds by diffuse reflectance infrared.

Diffuse reflectance infrared-PLS has a potential to derive a more specific predictive model targeted towards actual concentration prediction rather than just a classification of contamination levels. The aspect of the work discussed in this example was to prove that diffuse reflectance infrared-PLS could be used to predict total PAH from soil spectra inputs alone, while the resulting prediction errors are low enough for the diffuse reflectance infrared-MIR method to be useful.

PLS calibrations are usually built from a large number of samples, often >100, where the full sample set can be split into separate calibration and test sets. Usually we would need a reasonable sized calibration set to ensure robustness, and sufficient flexibility to identify and reject high spectral or analyte outliers and identify high-leverage outliers. If, however, we have a relatively small sample data set, we need to maximize the efficiency of the modelling used for calibration training and testing, usually by using the "leave-one-out" cross-validation method. This method works by predicting each sample in turn as an "unknown" from calibration models derived from the rest.

PLS cross-validation in small sample sets, while useful in extracting the maximum information from the available sample spectra and data, tends to give over-optimistic prediction validation errors and so "true" prediction, using separate calibration and test sets, are preferred if possible. The difficulty here is "How do we pick a very few of the most representative samples from a relatively small data set to form a robust calibration?", but still retain all the information from the full spectral data in this small calibration set. With regard to the number of samples available for calibration training with a small calibration set, there is a trade-off. Either we have enough calibration samples to fully model the spectral set but not enough samples to test the model, or a sufficient number of test samples but not enough to form a good calibration. One simple answer is to use a Euclidian distance based leverage method, derived from principal components analysis (PCA) of input data, to rank the samples to select the calibration samples.

Materials & Methods

Soils were passed through a 2 mm mesh, dried overnight at 40° C. and then ground using a ball mill for spectral analysis. Sub-samples were poured into aluminium microplates in a Bruker HTS infrared diffuse reflectance accessory (Ettlingen, Germany) and the top surfaces of the powdered soils levelled. Spectra were recorded on a Bruker Tensor 37 spectrometer from 8000 to 400 cm$^{-1}$ at a resolution of 4 cm$^{-1}$, but only the mid-infrared portion from 4000 to 500 cm$^{-1}$ or specific ranges within this portion was used for PLS analysis.

The spectrometer was equipped with a germanium-coated KBr beam splitter, a high intensity ceramic source, and a Mercury Cadmium Telluride (MCT) liquid nitrogen cooled detector. Background reference scans were performed by reflection from the surface of a silicon carbide (SiC) disk, assumed to have a reflectivity of 1 (100%), and the spectral intensities of the soils expressed in absorbance units [Absorbance=log(Reflectance$_{SiC}$/Reflectance$_{sample}$)].

Chemometrics analysis was carried out by exporting the spectra into chemometrics software, eg. Unscrambler™ Ver. 9.80 software (CAMO Software AS, Oslo, Norway). PLS options such as full "leave-one-out" cross-validation (Geladi and Kowalski 1986, Analytica Chimica Acta 185:1-17), baseline correction and other pre-processing are available with the use of these and similar software applications in an attempt to improve the models. As used herein, cross-validation regression statistics were expressed in terms of the coefficient of determination ($R^2$) and root mean square error of cross-validation (RMSECV). Alternatively, calibration sample selection was carried out by using the Unscrambler V9.8 "APSpectroscopy, StdSelect" add-on application. This application is based on a Euclidian distance based leverage method, derived from principal components analysis (PCA) of input data.

Experimental

1 Samples

The 16 PAH species, identified as contributing significantly to total PAH, the soils used for analysis, and the HPLC reference total PAH concentrations are presented in Table-1. For DRIFT spectra, soils were scanned as approximately 50 mg of dried and ground neat subsamples, in a HTS equipped Bruker Tensor 37 FTIR spectrometer in the full spectral range from 8000 to 400 cm$^{-1}$. Single beam spectra for each soil were referenced against a SiC reflecting disk and converted to Log(1/T) units (pseudo absorbance). Spectra and PAH data were entered into an Unscrambler Ver.9.8 (Software AS, Oslo, Norway) spreadsheet for PLS analysis.

TABLE 1

The 16 PAH species identified as being significant, the soils used for analysis and reference total PAH concentrations.

| | Acronym | PAH NAME |
|---|---|---|
| 1 | NAP | naphtalene |
| 2 | ACY | acenaphthylene |
| 3 | ACE | acenaphthene |
| 4 | FLU | fluorene |
| 5 | PHE | phenanthrene |
| 6 | ANT | anthracene |
| 7 | FLT | fluoranthene |
| 8 | PYR | pyrene |
| 9 | BaA | benzo (a) anthracene |
| 10 | CHY | chrysene |
| 11 | BbF | benzo (b) fluoranthene |
| 12 | BkF | benzo (k) fluoranthene |
| 13 | BaP | benzo (a) pyrene |
| 14 | DBA | dibenz (a,h) anthracene |
| 15 | PER | benzo (g,h,i) perylene |
| 16 | IND | indeno (1,2,3-c,d) pyrene |

| | Soil name | Total TPH |
|---|---|---|
| 1 | ABW08034 | 196 |
| 2 | AST08030 | 3648 |
| 3 | EWW08031 | 851 |
| 4 | IND08033 | 161 |
| 5 | K26_1 | 4 |
| 6 | K26_2 | 217 |
| 7 | K26_3 | 7579 |
| 8 | K26_4 | 39770 |
| 9 | K26_5 | 535 |
| 10 | K26_6 | 49 |
| 11 | K26_7 | 176 |
| 12 | K26_8 | 214 |
| 13 | K26_9 | 4807 |
| 14 | K26_10 | 7323 |
| 15 | K26_11 | 202 |
| 16 | K26_12 | 1542 |
| 17 | K26_13 | 2353 |
| 18 | K26_14 | 251 |
| 19 | K26_16 | 508 |
| 20 | K26_17 | 1673 |
| 21 | KUH08027 | 1395 |
| 22 | RAF08032 | 19270 |
| 23 | W35_2 | 178 |
| 24 | W35_3 | 143 |
| 25 | W35_4 | 382 |

2 Data Regression Analysis

PLS regression analysis was carried out on the soil DRIFT spectra by modelling the reference total PAH against the input spectral intensities by using the Unscrambler PLS-1 application. Calibration models were derived either by full "leave-one out" cross-validation, or as "true" prediction models using selected calibration samples. Calibration samples for the "true" predictions were selected from the full data set of samples using the User-defined add-on application APSpectroscopy StdSelect (Unscrambler V9.8, Camo Software AS, Oslo, Norway) and the "test" (validation) samples were the remaining set. The APSpectroscopy StdSelect application works by selecting the required number ($N_c$) of calibration samples from a full data set by ranking the PCA derived Euclidean distance leverages of all the samples and then selecting these from the highest $N_c$ samples.

Results

1. PLS Cross-Validation Prediction of Total PAH from Soil Drift Data

PLS cross-validation prediction of the full total PAH range with the NIR plus MIR spectra (6 factors, 10, 000-600 cm$^{-1}$)

was good, with an $R^2=0.92$ but the RMSECV error was high (2,452 ppm) and required 7 PLS factors. Reduction of the concentration range to 0-4,000 ppm and omission of the NIR spectral range to only the MIR (4,000-600 cm$^{-1}$) gave an $R^2=0.66$ and RMSECV=565 ppm for 6 PLS factors. It appeared that the larger spectral ranges were insensitive to low total TPH concentrations.

Figure 2:
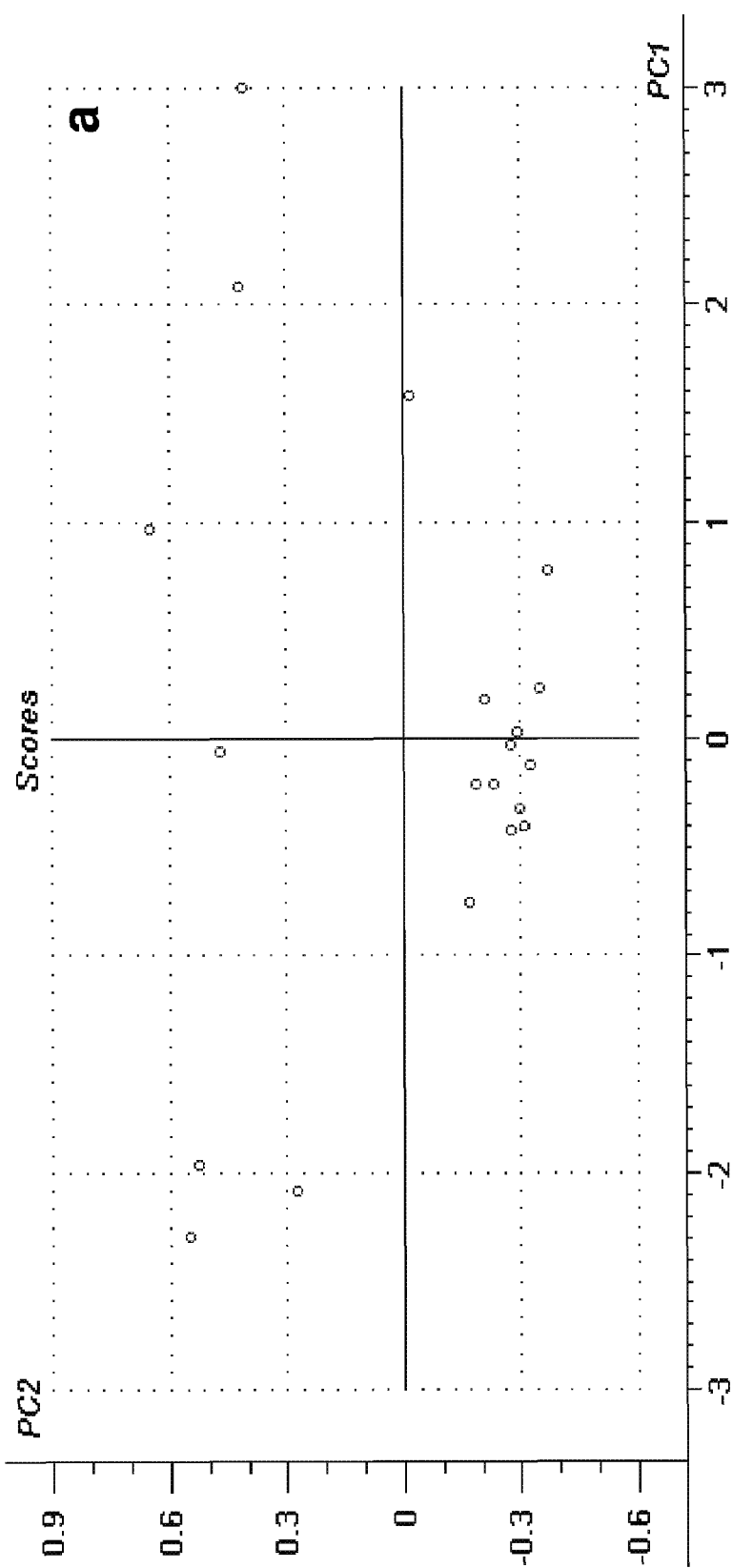
FIG. 2: PLS cross-validation regression plots of (a) score-2 versus score-1, (b) regression coefficients, (c) residual variance for each factor, and (d) cross-validation predicted total PAH in the range 0-4,000 mg/kg (ppm).
Figure 2:
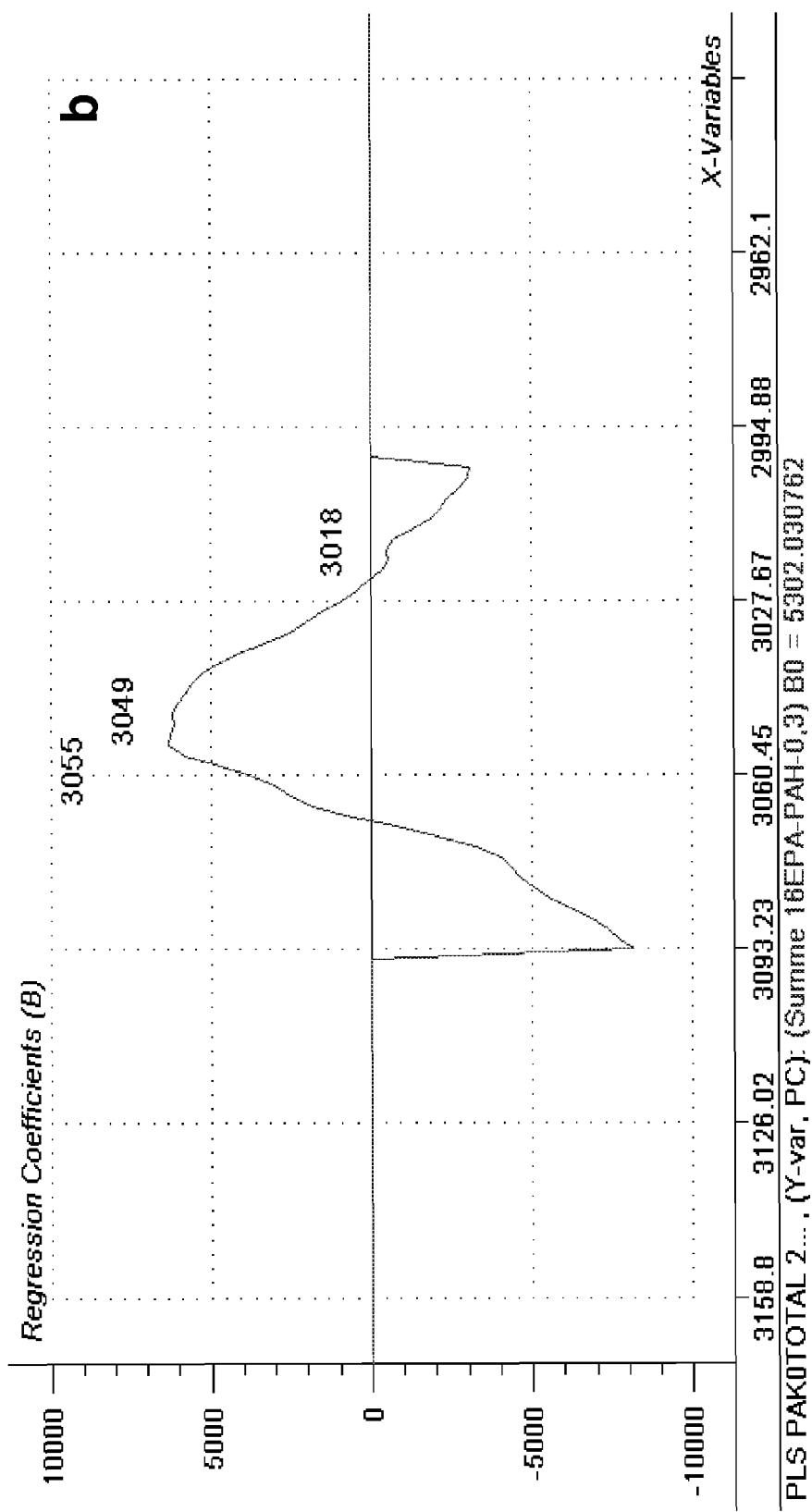
Figure 2:
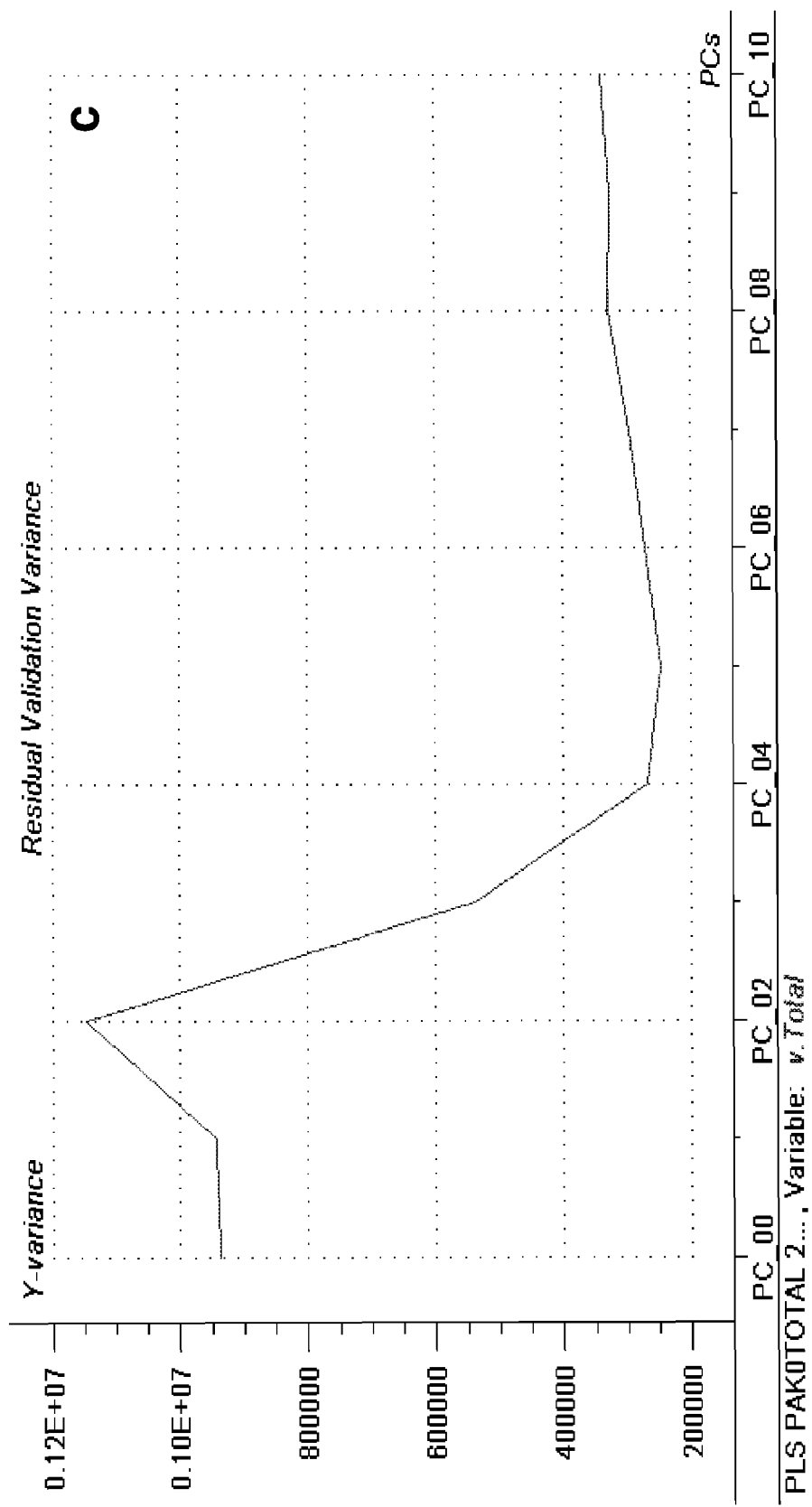
Figure 2:
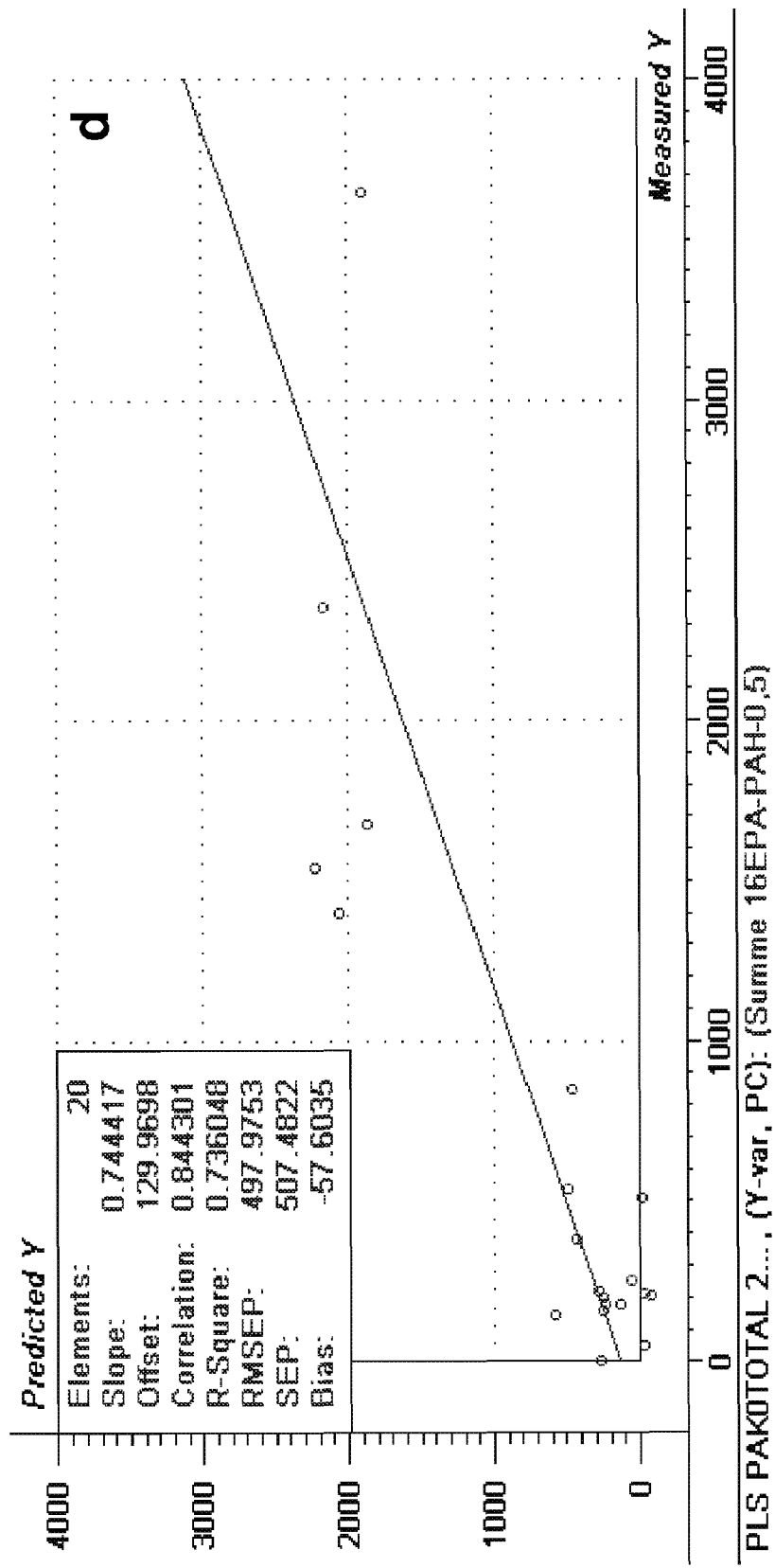
Figure 3:
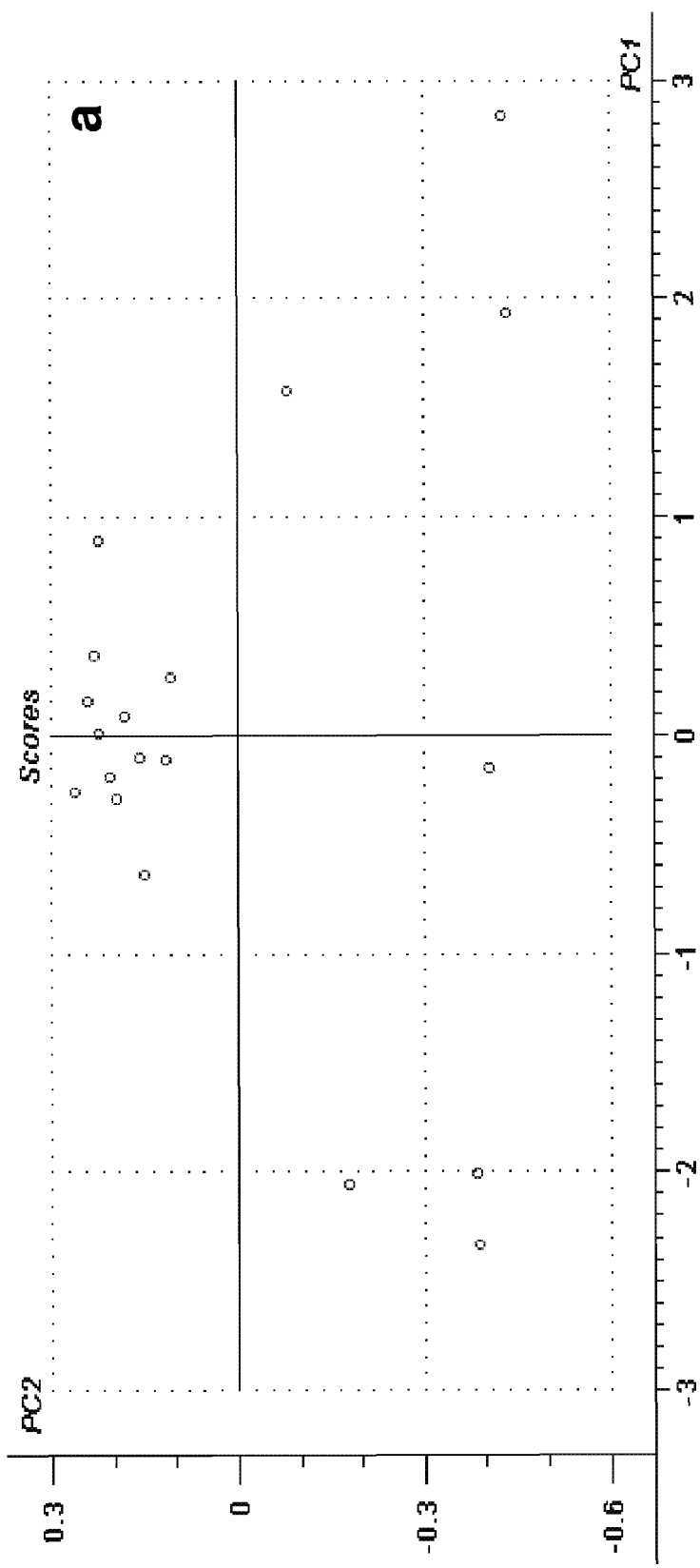
FIG. 3: PLS cross-validation regression plots of (a) score-2 versus score-1, (b) regression coefficients, (c) residual variance for each factor, and (d) cross-validation predicted total PAH in the range 0-2,500 mg/kg (ppm).
Figure 3:
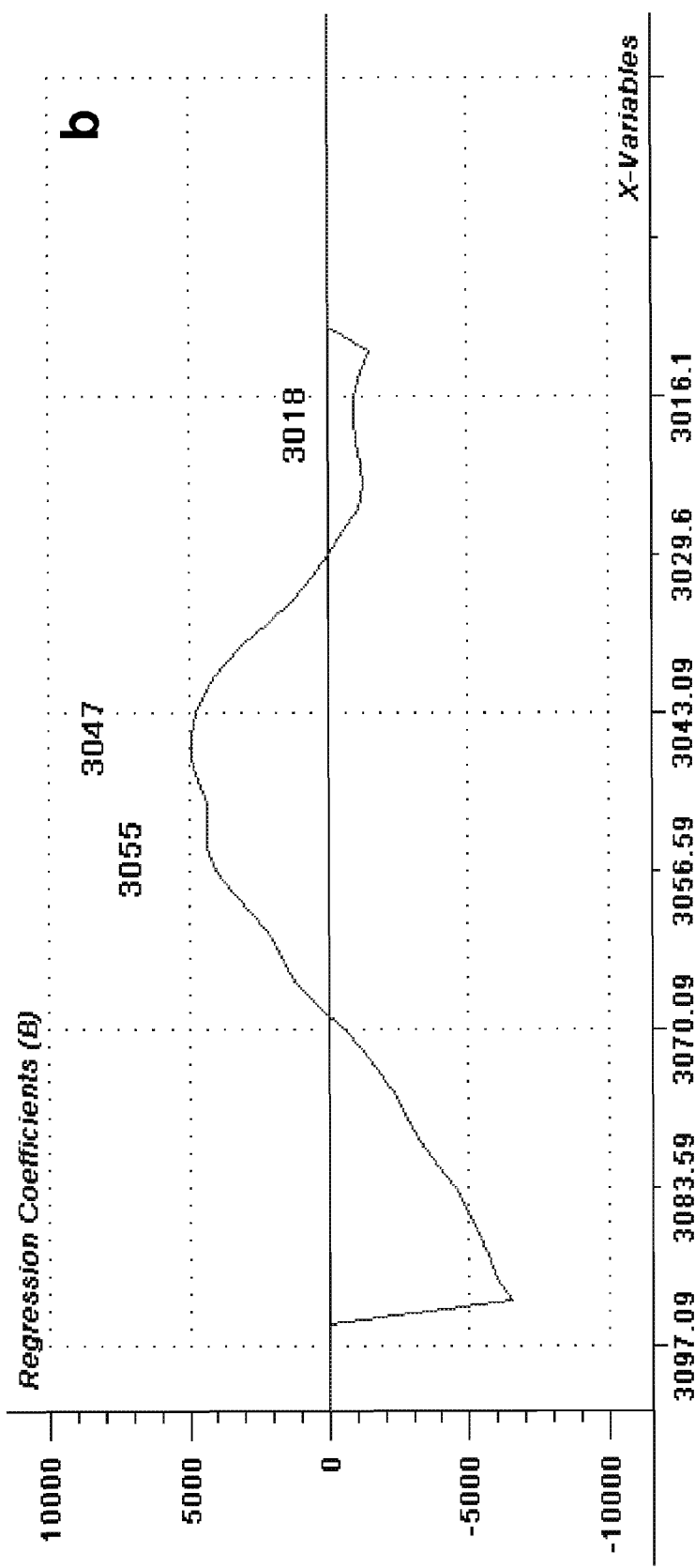
Figure 3:
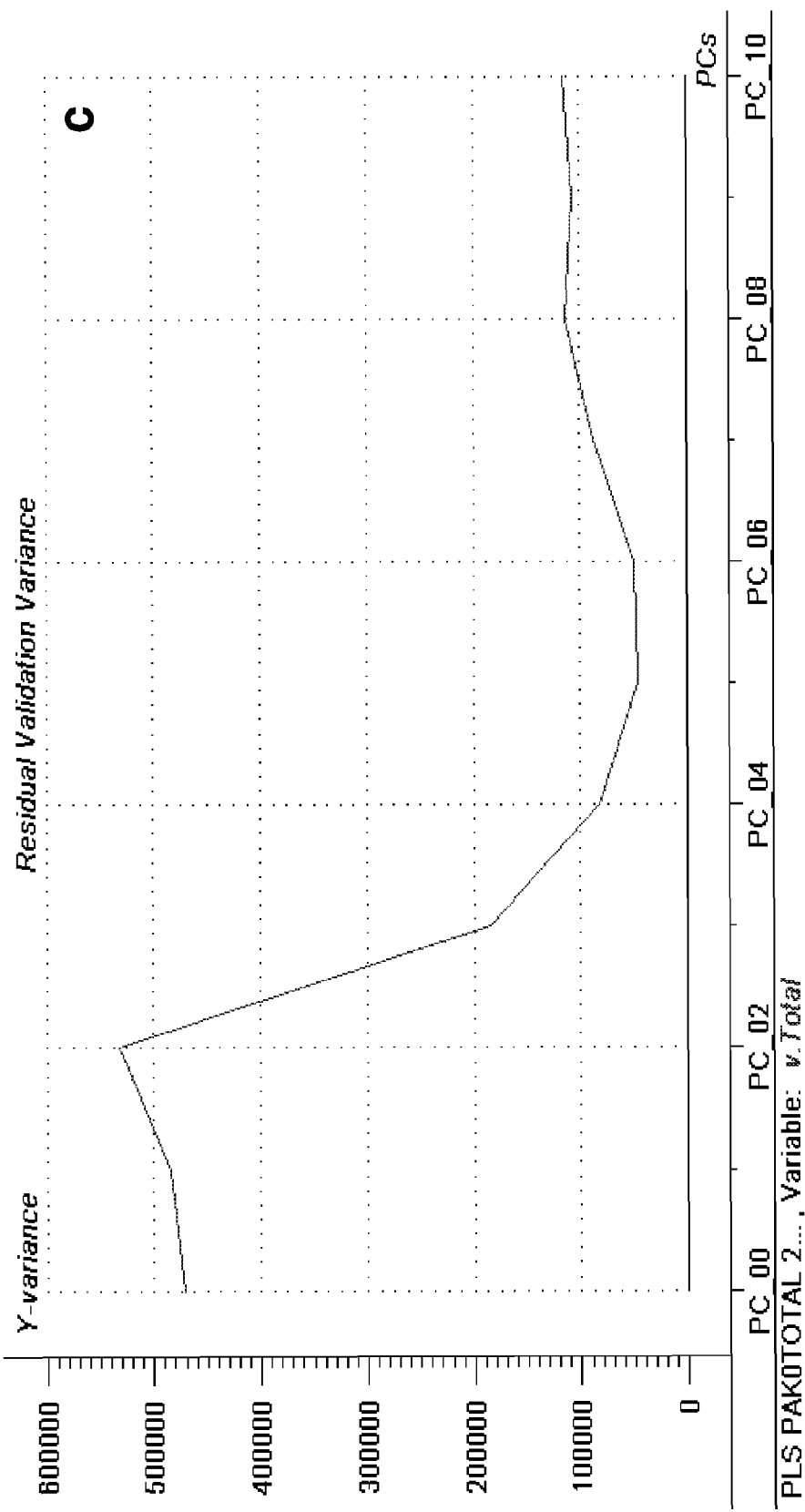
Figure 3:
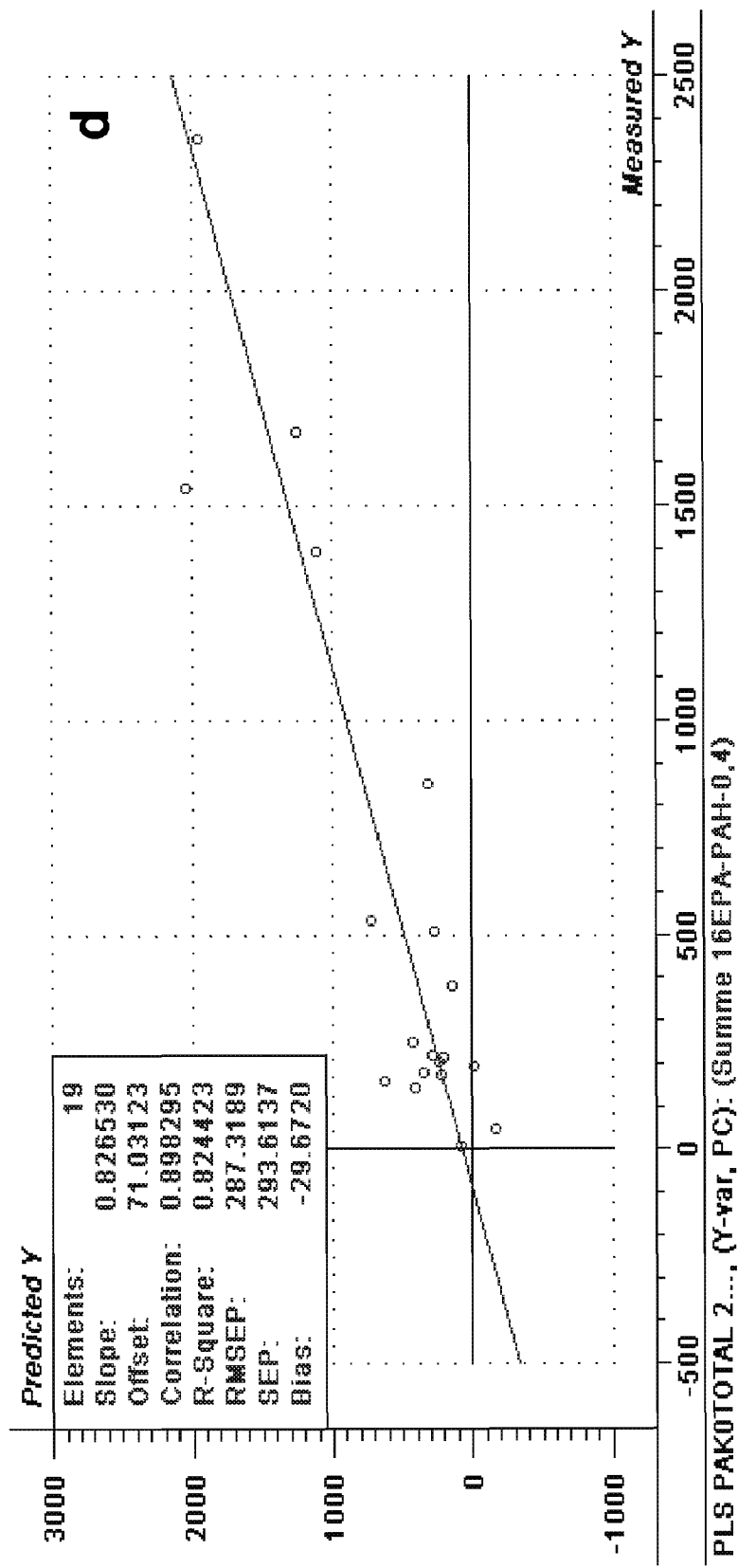

Further calibrations were run using a very much reduced spectral range to only the aromatic =C—H stretching frequencies near 3047 and 3022 cm$^{-1}$. FIGS. 1, 2 and 3 describe the regression results for the cross-validation of a range of total PAH concentrations: 0-40,000 ppm, 0-4,000 ppm and 0-2,500 ppm, respectively. The regression for the full concentration range resulted in an $R^2=0.99$ and an RMSECV=1,061 ppm for 3 factors. Reducing the concentration range to 0-4,000 gave a reduced accuracy, with an $R^2=0.74$ using 5 factors and the same frequencies, but a better RMSECV=498 ppm. Lowering the concentration range even further to 0-2,500 ppm gave an even lower RMSECV=287 ppm for 4 factors and with an $R^2=0.82$. Increasing the number of PLS factors to 5 improved the RMSECV to 216 ppm, but with increased risk of over-fitting the calibration.

Calibration over-fitting results in models that are specific to only the current set of data being used. The model may therefore be unstable and lack robustness because many redundant frequencies are not available to account for outliers. It is uncertain whether these cross-validation results can be considered as indicating good or poor prediction potential. The $R^2$ and RMSECV values for the 0-2,500 ppm range were indicative of being sufficient for RMSECV below 300 ppm. When considering the 0-1,000 ppm range, samples EWW08031 (851/310 ppm), K26-16 (508/265 ppm) and W35-4 (382/149 ppm) gave false negatives (indicated as reference/predicted). Two sample in the 0-300 ppm range (W35-3 (143/430 ppm), K26-1 (4/188 ppm) gave false positives. Interestingly, when regressing the full data set, in spite of the high overall RMSECV, there was only one false negative in the 0-300 ppm range; sample W35-4 with a reference value of 382 ppm and predicted value of 259 ppm. In spite of these reservations, the results of the analysis confirmed the most important spectral regions to be used in future PLS developments, the most likely chemistry in the samples correlating with the PAHs and a likely-hood of success with large data sets.

2. PLS Prediction of Total PAH from Selected Soil Drift Calibration Samples

Figure 4:
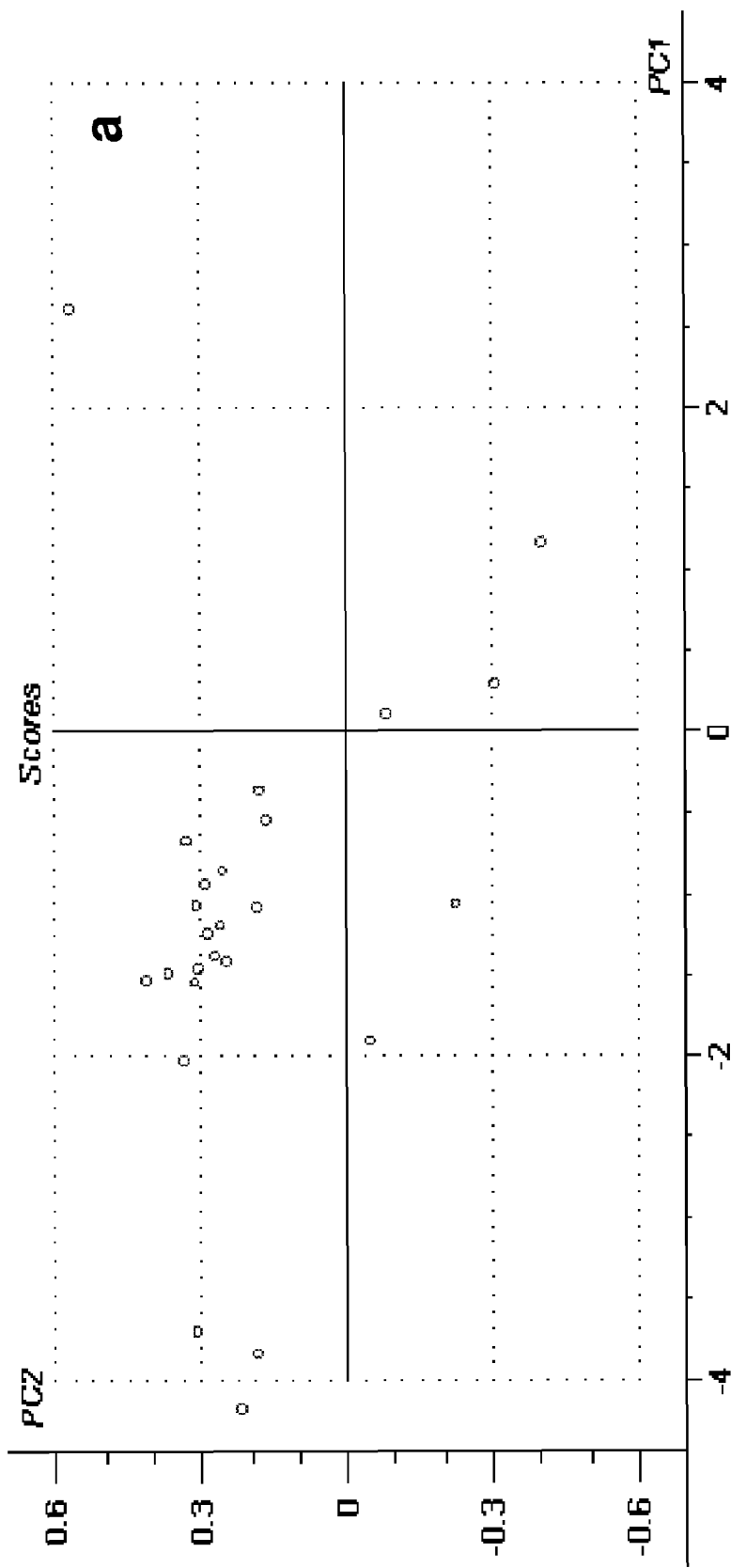
FIG. 4: PLS prediction regression plots of (a) score-2 versus score-1, (b) regression coefficients, (c) residual variance for each factor, and (d) predicted total PAH for each soil for the full soil set. The calibration model was based on soil DRIFT spectra from 5 samples using a Euclidean distance PCA leverage method.
Figure 4:
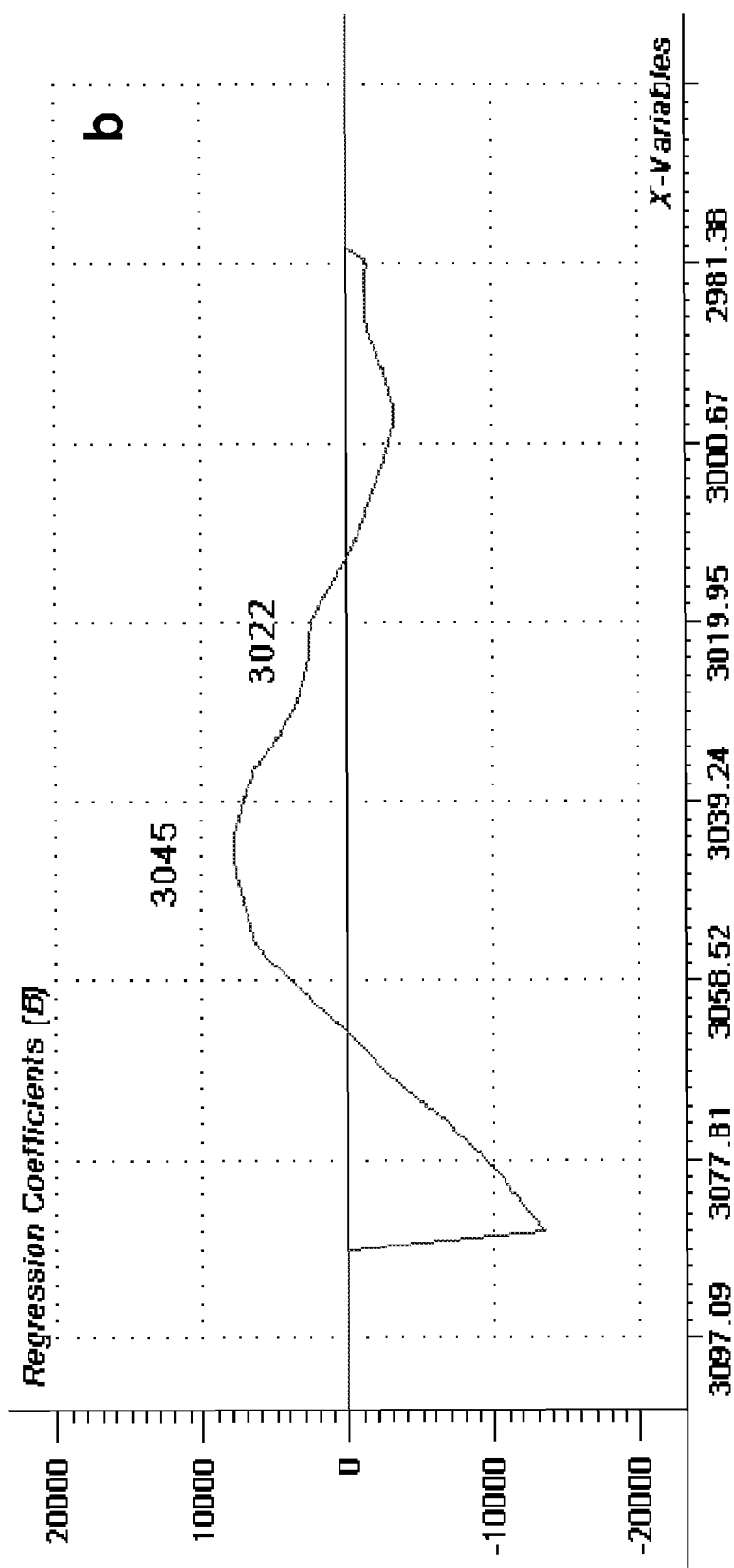
Figure 4:
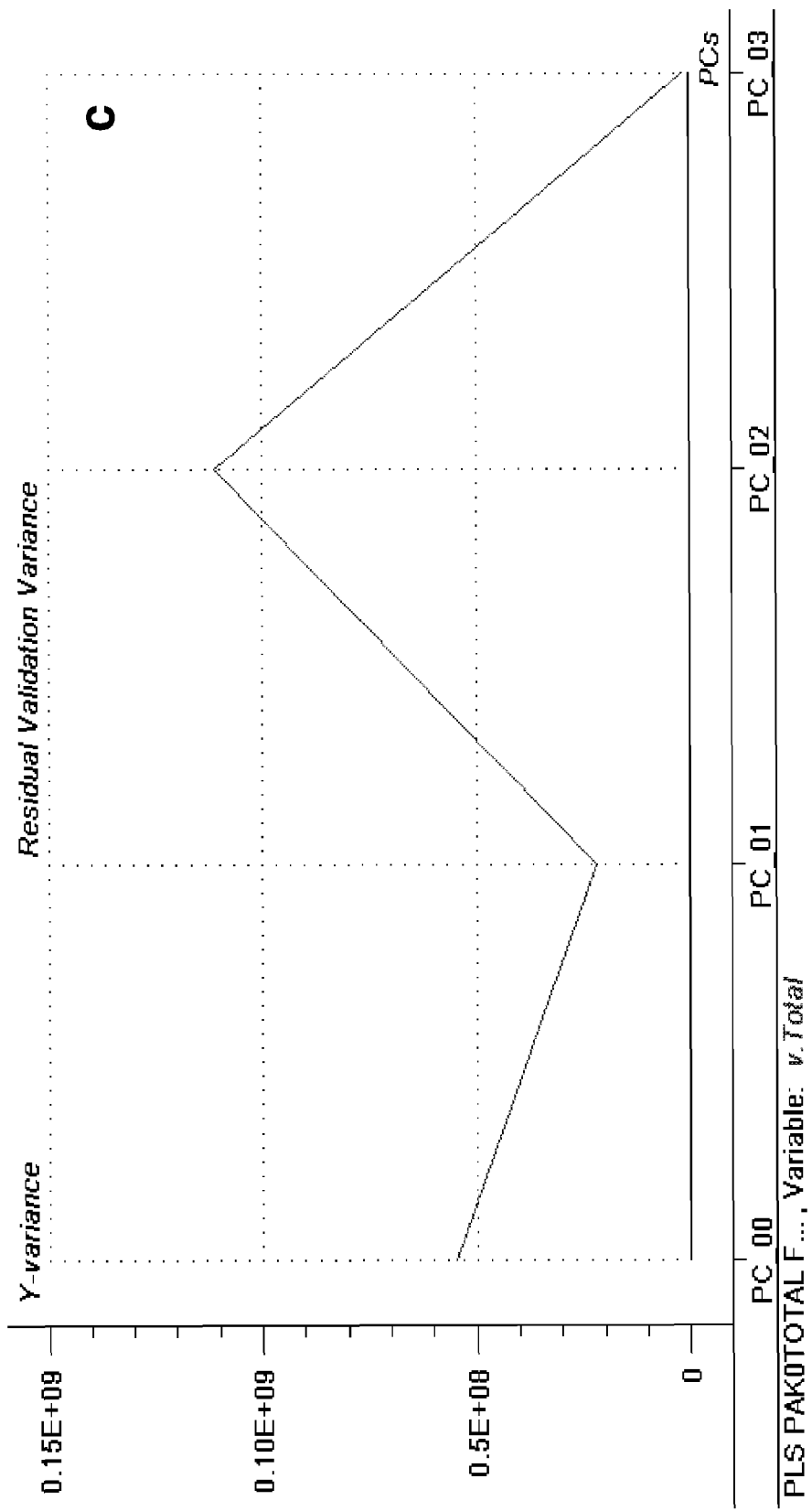
Figure 4:
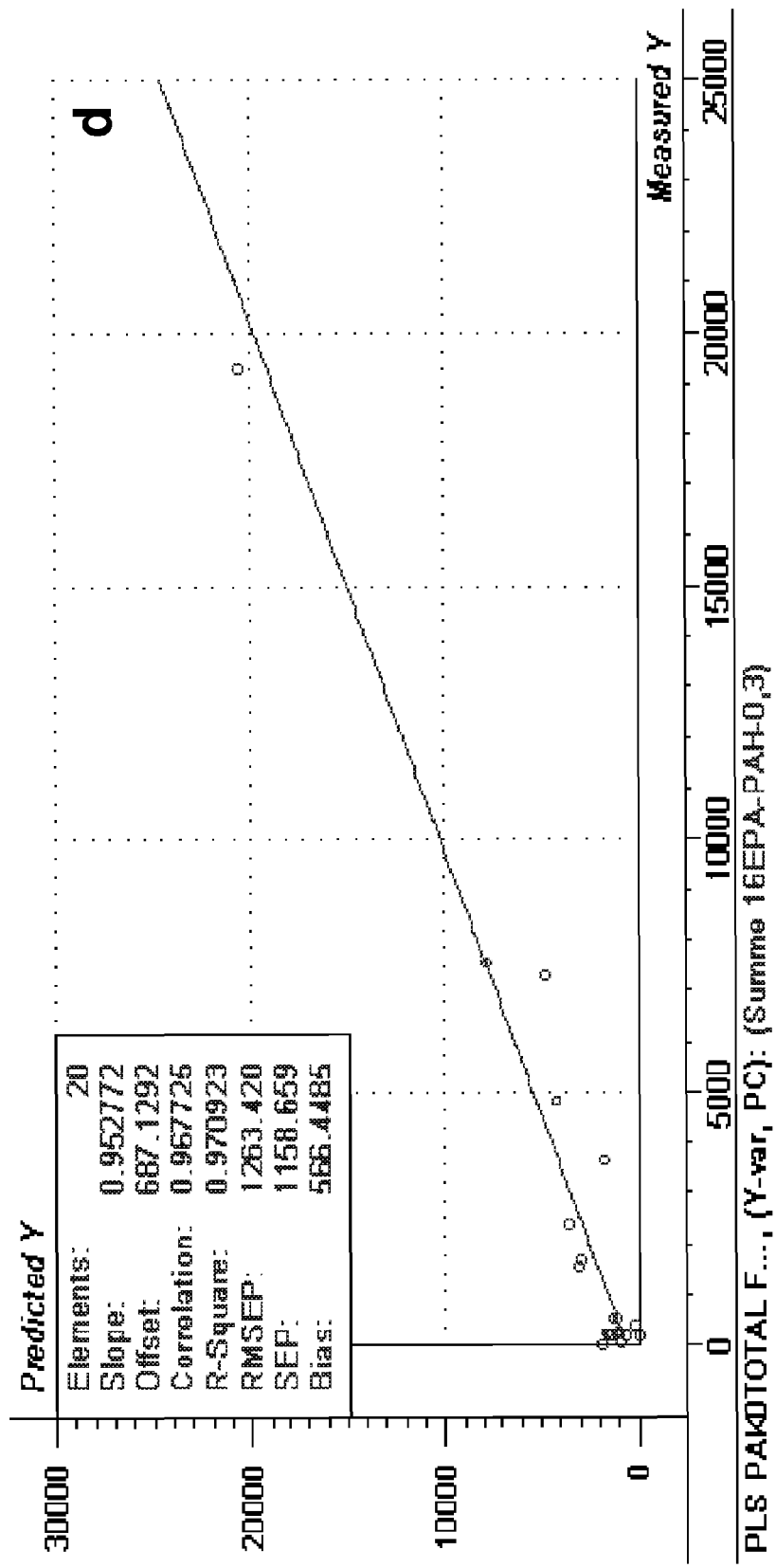

The APSpectroscopy StdSelect application in Unscrambler (see Experimental above) was used to select five calibration samples (EWW08031, IND08033, KUH08027, W35-3 and K26-4) for the PLS calibration model, with the remaining 20 samples being allocated to the "test" set. This resulted in prediction regression with an $R^2=0.97$ and RMSEP=1,263 ppm. FIG. 4 depicts the results of the PLS prediction of HPLC total PAH data using the five soil DRIFT calibration samples described above.

Again, the main peaks correlating with total PAH were at 3047 and 3022 cm$^{-1}$, typical of aromatic compounds. While sample W35-4 was the only sample to be predicted as a false negative (382/194 ppm) in the 0-1,000 ppm range, there was a high offset (687 ppm) in low total PAH values, rendering this assessment uncertain.

Conclusions

DRIFT PLS regression models were shown to be able to predict total PAH concentrations in whole neat soils in the concentration range of 0-40,000 ppm. The optimum frequencies near 3047 cm$^{-1}$ and 3022 cm$^{-1}$ were consistent with the assignment of PAH aromatic =C—H vibration. Use of this peak for PAH prediction appears to overcome, to a large extent, problems with contributions from natural soil organic matter.

While cross-validation for the full concentration range resulted in an excellent $R^2=0.99$, the RMSECV was high at 1,061 ppm. Reducing the concentration range to 0-2,500 ppm reduced the RMSECV to 287 ppm, close to the limit of 300 ppm. Only three samples in the 0-1,000 ppm range were predicted as false negatives, showing that the DRIFT method is potentially capable of achieving useful accuracies for total PAH concentrations in whole, neat soils.

An excellent regression was also obtained using a calibration set of 5 Euclidean distance leverage-selected samples and a prediction set of the remaining 20 samples. This resulted in an $R^2=0.97$ and prediction error of 1,263 ppm for the full concentration range. While not as good as the cross-validation results, the results confirmed that useful, robust calibrations for prediction were possible.

Example 2

PLS Calibrations for Individual PAH Compounds in Soils

There is often a need to be able to predict the concentrations of individual PAH compounds, in addition to total PAH, e.g. in response to a preference of remediation companies for individual PAH predictions rather than just total PAH concentrations. There is therefore a question as to the ability of the proposed infrared PLS method to address this need, particularly for some of the minor but relatively hazardous compounds such as BaP (tens of mg/Kg), as the calibration error for total PAH may be less than 300 mg/Kg for a range of 0-2,500 mg/Kg. Nevertheless, there may be an advantage as a rapid screening tool even though individual PAH may not be predicted with the highest accuracy.

According to the USEPA, 16 main PAH compounds have been identified as posing hazardous risk in the environment, herein called polynuclear aromatics (see Table 1). Concentrations in the environment are usually in the sub-ng/cm$^3$ amounts. It was suggested that PLS regression for the individual PAHs, particularly Naphthalene (2-ring), Phenanthrene (3-ring), Fluoranthene (4-ring), and Benzo(b)fluoranthene (5-ring) could also be viable. This example presents the results of tests to determine PLS regression models for each of the determined PAH compounds.

Experimental

Spectra

A total of 25 soils containing the 16 PAH compounds were scanned on a Bruker FTIR as previously reported in the full spectral range from 8000 to 670 cm$^{-1}$. Spectra were entered into an Unscrambler spreadsheet for PCA and PLS regression analysis.

Data Analysis

PCA and PLS regression analysis was carried out using the Unscrambler software V9.8 (CAMO Software AS, Oslo, Norway). Redundant spectral frequencies, or those that did not contribute significantly to the regression, were selectively removed from analysis in order to optimize the models. Outliers were removed from the initial 25 samples.

Results

PLS regression results are depicted in Table 2 below for each of the individual PAH compounds using the reference HPLC data in the models.

TABLE 2

Results of PLS regression for individual PAH determination

| | PAH | PAH Concentration Range (mg/Kg) | Number of samples | Number of outlier samples | PLS Factors | $R^2$ | RMSECV (mg/Kg) | PLS model MIR peaks (cm$^{-1}$) | | | |
|---|---|---|---|---|---|---|---|---|---|---|---|
| 1 | Naphthalene (NAP) | 11000 | 24 | | 3 | 0.966 | 413 | | | 3045 | 3021 |
| 2 | Acenaphthylene (ACY) | | | | | | | | | | |
| 3 | Acenaphthene (ACE) | 5100 | 24 | | 3 | 0.973 | 176 | 3053 | | 3047 | |
| 4 | Fluorene (FLU) (1-OL) | 2700 | 24 | 1 | 4 | 0.968 | 100 | 3055 | 3049 | | 3022 |
| 5 | Phenanthrene (PHE) | 8000 | 24 | | 4 | 0.951 | 367 | 3055 | 3051 | | 3020 |
| 6 | Anthracene (ANT) | 360 | 22 | 2 | 3 | 0.973 | 12.5 | | 3051 | 3047 | 3021 |
| 7 | Fluoranthene (FLT) | 5900 | 24 | 1 | 3 | 0.984 | 165 | | 3051 | 3047 | |
| 8 | Pyrene (PYR) | 3650 | 25 | | 3 | 0.969 | 136 | | 3049 | | 3020 |
| | Pyrene (PYR) repeat | 3500 | 24 | 1 | 3 | 0.983 | 103 | | | | |
| 9 | Benzo-anthracene (BaA) | 550 | 24 | | 3 | 0.981 | 32 | 3055 | | | |
| | Benzo-anthracene (BaA) repeat | 120 | 23 | 1 | 6 | 0.797 | 16.5 | | | | |
| 10 | Chrysene (CHY) | 560 | 24 | 1 | 3 | 0.955 | 24.4 | 3053 | | 3045 | |
| 11 | Benzo (b) fluoranthene (BbF) | 40 | 23 | 2 | 3 | 0.919 | 2.7 | 3053 | | | |
| 12 | Benzo (k) fluoranthene (BkF) | 32 | 24 | 1 | 3 | 0.702 | 4.17 | 3053 | | 3047 | 3010 |
| 13 | Benzo-pyrene (BaP) | 73 | 25 | | 4 | 0.805 | 9.25 | | 3051 | | 3020 | 740 |
| 14 | Dibenz (a,h) anthracene (DBA) | 7.1 | 23 | 2 | 3 | 0.398 | 1.43 | 3055 | | | |
| 15 | Benzo (g,h,i) Perylene (PER) | | | | | | | | | | |
| 16 | Indeno (1,2,3-c,d) pyrene (IND) | 14 | 24 | 1 | 4 | 0.59 | 2.59 | 3057 | | | |

RMSECV = Root Mean Square Error in Cross-Validation
Peaks in bold are the strongest peaks. Peaks not in bold are observed as weak shoulders.

CONCLUSIONS

The results presented above suggest that the spectral information of individual PAHs, particularly near 3045 cm$^{-1}$, contains sufficient information to allow them to be quantified by diffuse reflectance mid-infrared spectroscopy. Most individual PAH calibrations appear to be successful but the lower concentration, higher ring number, PAHs are more difficult to determine accurately. The PLS modelling for BaP and some of the minor PAHs also look good, but correlation with other major PAHs should not be discounted. Diffuse reflection infrared spectroscopy with PLS regression therefore appears to be feasible for individual PAH compounds, depending on concentration ranges, chemistry and molecular structure.

The invention claimed is:

1. A method for determining PAH concentration in a solid state sample, which method comprises
    a) exposing the sample to diffuse reflectance infrared spectroscopy,
    b) recording at least one spectroscopic parameter of infrared diffuse reflection of said sample, which is a signal obtained at one or more frequencies within a range of frequencies (+/−10 cm$^{-1}$) selected from the group consisting of 3000-3100 cm$^{-1}$, 740, 777, 814, 842, 1430, 1510, 1600, 4055- 4056, 4642-4646, 5924, and 5951- 5953 cm$^{-1}$, and
    c) performing data analysis by correlating the at least one spectroscopic parameter with variables of a trained multivariate calibration model related to PAH concentrations, thereby determining PAH concentrations in the sample.

2. The method according to claim 1, wherein one or more signals are obtained at frequencies about those selected from the group consisting of 3022, 3047 and 3055 cm$^{-1}$.

3. The method according to claim 1, wherein said multivariate data analysis is by multivariate regression analysis.

4. The method according to claim 3, wherein said multivariate data analysis is by partial least square (PLS) regression analysis.

5. The method according to claim 1, wherein a system is used that is trained by employing either of
    a) a calibration data set,
    b) a calibration data set after removal of any outlier samples identified by the use of PLS score versus score plots, or
    c) selection of separate calibration and test sets.

6. The method according to claim 5, wherein the separate calibration and test sets are selected by using a PCA Euclidean distance leverage method.

7. The method according to claim 1, which further comprises an internal calibration step performed by either training by cross-validation of the sample data or prediction of a test set from a selected calibration set.

8. The method according to claim 7, which further comprises upgrading the calibration by adding further calibration samples of known PAH concentrations, to generate a recalibrated model for determining PAH concentration.

9. The method according to claim 1, for calibration purposes to predict concentrations of either total PAH or of individual PAH compounds.

10. The method according to claim 9, wherein a method of training a calibration system is employed, which comprises
    a) preparing a panel of diffuse reflectance infrared spectra obtained by solid state spectroscopy of different samples, having PAH concentrations at various levels in the range from 0 to 50,000 ppm, and
    b) correlating the spectra with the PAH concentration in the samples.

11. The method according to claim 1, wherein the total PAH concentration is determined.

12. The method according to claim 1, wherein the concentration of at least one individual PAH selected from polynuclear aromatics is determined.

13. The method according to claim 12, wherein said sample is a soil, rock, solid waste sample, or a material derived from such sample, which sample is untreated as taken from the environment and optionally pretreated by drying, grinding and sieving.

14. The method The method according to claim 12, which is an in-field or in-process determination method.

15. A method for determining PAH concentration in a solid state sample, which method comprises
    a) exposing the sample to DRIFT spectroscopy,
    b) recording at least one spectroscopic parameter of MIR reflection of said sample, which is a signal obtained at frequencies ranging from 3000 to 3100 cm$^{-1}$, and c) performing multivariate data analysis by correlating the at least one spectroscopic parameter with variables of a trained system related to PAH concentrations, thereby obtaining quantitative calibration modelling and determination of PAH in the sample.

16. The method according to claim 15, wherein one or more further signals are obtained at frequencies selected from the group consisting of NIR and MIR ranges at about 5953 cm$^{-1}$ (NIR), 4646 cm$^{-1}$ (NIR), 4065 cm$^{-1}$ (NIR), 3047 cm$^{-1}$ (MIR) and 3022 cm$^{-1}$ (MIR).

* * * * *

UNITED STATES PATENT AND TRADEMARK OFFICE
CERTIFICATE OF CORRECTION

| | | |
|---|---|---|
| PATENT NO. | : 9,134,227 B2 | Page 1 of 1 |
| APPLICATION NO. | : 13/504977 | |
| DATED | : September 15, 2015 | |
| INVENTOR(S) | : Janik et al. | |

It is certified that error appears in the above-identified patent and that said Letters Patent is hereby corrected as shown below:

On the Title Page item "[73] Assignee", please delete "UNIVERSITÄT FÜR BODENKULTER WIEN", and insert --UNIVERSITÄT FÜR BODENKULTUR WIEN--.

Signed and Sealed this
First Day of March, 2016

Michelle K. Lee
*Director of the United States Patent and Trademark Office*